(12) United States Patent
Takemura et al.

(10) Patent No.: US 6,462,040 B1
(45) Date of Patent: Oct. 8, 2002

(54) CIS-SUBSTITUTED AMINOCYCLOPROPANE DERIVATIVE

(75) Inventors: Makoto Takemura; Youichi Kimura; Hisashi Takahashi; Yohhei Ishida, all of Tokyo (JP)

(73) Assignee: Daiicho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/907,909

(22) Filed: Jul. 19, 2001

Related U.S. Application Data

(62) Division of application No. 09/214,433, filed as application No. PCT/JP97/02411 on Jul. 11, 1997, now Pat. No. 6,391,889.

(30) Foreign Application Priority Data

Jul. 12, 1996 (JP) ............................................... 8-182939

(51) Int. Cl.⁷ ........................ A61K 31/53; A61K 31/47; C07D 498/12; C07D 215/233
(52) U.S. Cl. .................... 514/230.2; 514/312; 544/101; 546/156
(58) Field of Search ........................ 544/101; 546/156; 514/230.2, 312

(56) References Cited

U.S. PATENT DOCUMENTS 4,954,507 A    9/1990  Weber et al.
5,284,842 A    2/1994  Petersen et al.
5,380,874 A    1/1995  Hayakawa et al.

FOREIGN PATENT DOCUMENTS

| JP | 59-67269 | 4/1984 |
| JP | 62-234082 | 10/1987 |
| JP | 3-502452 | 6/1991 |
| JP | 5-132479 | 5/1993 |
| JP | 7-285865 | 10/1995 |
| JP | 7-300472 | 11/1995 |
| JP | 8-48629 | 2/1996 |
| JP | 8-277284 | 10/1996 |
| JP | 9-67368 | 3/1997 |

*Primary Examiner*—Patricia L. Morris
(74) *Attorney, Agent, or Firm*—Sughrue Mion, PLLC

(57) ABSTRACT

The present invention relates to an antimicrobial compound having high safety as well as potent antimicrobial activity on a broad range of microorganisms represented by the following formula:

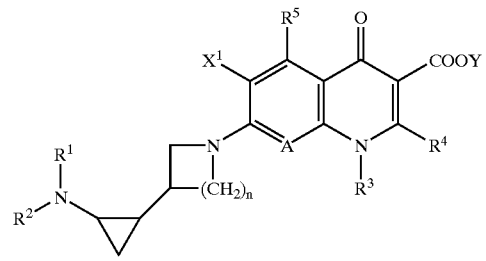

10 Claims, No Drawings

CIS-SUBSTITUTED AMINOCYCLOPROPANE DERIVATIVE

This is a divisional of application Ser. No. 09/214,433 filed Jan. 6, 1999, now U.S. Pat. No. 6,391,889, which is a 371 of PCT/JP97/02411 filed Jul. 11, 1997, the disclosure of which is incorporated herein by reference.

TECHNICAL FIELD

This invention relates to an antimicrobial compound useful as a drug for humans, animals or fishes or an antimicrobial preservative and an antimicrobial agent or preparation containing the same.

BACKGROUND ART

Since the discovery of Norfloxacin, improvements have been added to synthetic quinolone antimicrobial agents in antimicrobial activity and in pharmacokinatics, and many compounds have been launched for clinical use as a chemotherapeutic agent effective on all most all systemic infectious diseases.

However, low sensitive bacteria resistant to the synthetic quinolone antimicrobial agents hive recently been increasing in the clinical field. For example, bacteria resistant to drugs other than synthetic quinolone antimicrobial agents have come to acquire resistance to synthetic quinolone antimicrobial agents, as exemplified by *Staphylococcus aureus* insensitive to β-lactam antibiotics (MRSA). Therefore, more effective drugs have been keenly demanded in the field of clinics.

Further, it has been revealed that synthetic quinolone antimicrobial agents tend to involve side effects, such as induction of convulsion in a combined use with a non-steroid antiinflammatory agent, and phototoxicity. Therefore, development of safer synthetic quinolone antimicrobial agents has been sought.

DISCLOSURE OF THE INVENTION

In the light of these circumstances, the inventors have conducted extensive investigation for the purpose of providing excellent compounds fulfilling the above demands. As a result, they have found that cis-substituted aminocyclopropane derivatives represented by the following formula (I) and their salts have broad antimicrobial spectra, exhibiting potent antimicrobial activity particularly on Gram positive bacteria, especially quinolone-resistant bacteria including MRSA, and also show satisfactory in pharmacokinatics and safety.

The present invention relates to a compound represented by formula (I) shown below, its salt and their hydrates:

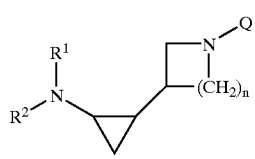

(I)

wherein $R^1$ and $R^2$ each independently represents a hydrogen atom or an alkyl group having 1 to 6 carbon atoms which may be substituted with one or more substituents selected from the group consisting of a hydroxyl group, a halogen atom, an alkylthio group having 1 to 6 carbon atoms, and an alkyloxy group having 1 to 6 carbon atoms; n represents an integer of 1 to 3; Q represents a partial structure having formula:

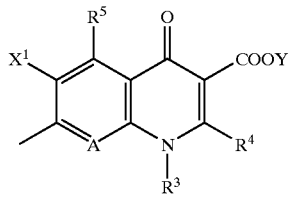

wherein $R^3$ represents an alkyl group having 1 to 6 carbon atoms, an alkenyl group having 2 to 6 carbon atoms, a halogenoalkyl group having 1 to 6 carbon atoms, a substituted or unsubstituted cycloalkyl group having 3 to 6 carbon atoms, a substituted or unsubstituted aryl group, a substituted or unsubstituted heteroaryl group, an alkoxyl group having 1 to 6 carbon atoms, or an alkylamino group having 1 to 6 carbon atoms; $R^4$ represents a hydrogen atom or an alkylthio group having 1 to 6 carbon atoms; $R^3$ and $R^4$ may be taken together with part of the mother skeleton to which they are bonded to form a cyclic structure that may contain a sulfur atom as a ring constituting atom and/or may be substituted with an alkyl group having 1 to 6 carbon atoms; $R^5$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may be substituted with one or more substituents selected from the group consisting of a formyl group, an alkyl group having 1 to 6 carbon atoms, and an acyl group having 2 to 5 carbon atoms; $X^1$ represents a halogen atom or a hydrogen atom; and A represents a nitrogen atom or a partial structure represented by formula (II):

(II)

wherein $X^2$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms, in which the amino group may be substituted with one or more substituents selected from the group consisting of a formyl group, an alkyl group having 1 to 6 carbon atoms and an acyl group having 2 to 5 carbon atoms; and $X^2$ and $R^3$ may be taken together with part of the mother skeleton to which they are bonded to form a cyclic structure that may contain an oxygen atom, a nitrogen atom or a sulfur atom as a ring constituting and/or may be substituted with an alkyl group having 1 to 6 carbon atoms;

and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group having 1 to 6 carbon atoms in the alkyl moiety thereof;

and the two substituents on the cyclopropane ring,

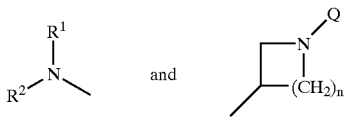

are in a cis-configuration.

The present invention also relates to:

a compound of formula (I), wherein Q is a partial structure represented by formula:

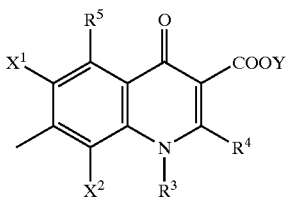

wherein $R^3$, $R^4$, $R^5$, $X^1$, $X^2$, and Y are as defined above, or a salt or hydrate thereof or a hydrate of the salt;

a compound of formula (I), wherein Q is a 6-carboxy-9-fluoro-2,3-dihydro-3-(S)-methyl-7-oxo-7H-pyrido[1,2,3-de][1,4]benzoxazin-10-yl group of formula:

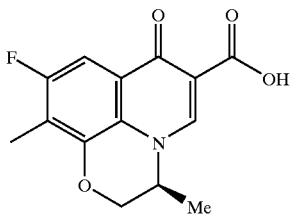

or a salt or hydrate thereof or a hydrate of the salt;

a compound of formula (I), wherein Q is a 8-amino-6-carboxy-9-fluoro-2,3-dihydro-3-(S)-methyl-7-oxo-7H-pyrido[1,2,3-de][1,4]benzoxazin-10-yl group of formula:

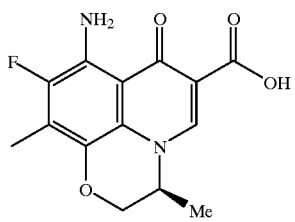

or a salt or hydrate thereof or a hydrate of the salt;

a compound of formula (I), wherein Q is a 5-amino-3-carboxy-6-fluoro-1-[2-(S)-fluoro-1-(R)-cyclopropyl]-1,4-dihydro-8-methoxyl-4-oxoquinolin-7-yl group of formula:

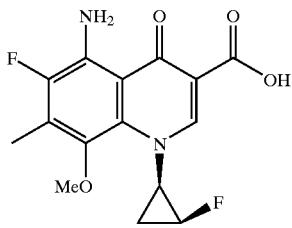

or a salt or hydrate thereof or a hydrate of the salt;

a compound of formula (I), wherein Q is a 5-amino-3-carboxy-6-fluoro-1-[2-(S)-fluoro-1-(R)-cyclopropyl]-1,4-dihydro-8-methyl-4-oxoquinolin-7-yl group of formula:

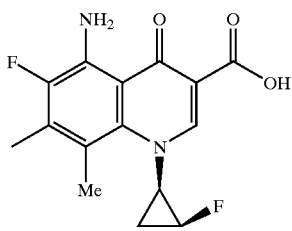

or a salt or hydrate thereof or a hydrate of the salt;

a compound of formula (I), wherein Q is a 3-carboxy-6-fluoro-1-[2-(S)-fluoro-1-(R)-cyclopropyl]-1,4-dihydro-8-methoxyl-4-oxoquinolin-7-yl group of formula:

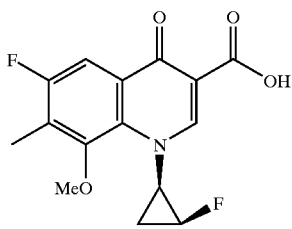

or a salt or hydrate thereof or a hydrate of the salt;

a compound of formula (I), wherein n is 2, or a salt or hydrate thereof or a hydrate of the salt;

a compound of formula (I), wherein $R^1$ and $R^2$ are each a hydrogen atom, or a salt or hydrate thereof or a hydrate of the salt;

a compound of formula (I), wherein $R^3$ is a halogenocyclopropyl group, or a salt or hydrate thereof or a hydrate of the salt;

a compound of formula (I), wherein $R^3$ is a 1,2-cis-2-halogenocyclopropyl group, or a salt or hydrate thereof or a hydrate of the salt;

a compound of formula (I), wherein $R^3$ is a stereochemically pure substituent, or a salt or hydrate thereof or a hydrate of the salt;

a compound of formula (I), wherein $R^3$ is a (1R,2S)-2-halogenocyclopropyl group, or a salt or hydrate thereof or a hydrate of the salt;

a compound of formula (I), wherein $R^3$ is a (1R,2S)-2-fluorocyclopropyl group, or a salt or hydrate thereof or a hydrate of the salt;

a compound of formula (I), wherein $X^1$ is a halogen atom, or a salt or hydrate thereof or a hydrate of the salt;

a compound of formula (I), wherein $X^1$ is a fluorine atom, or a salt or hydrate thereof or a hydrate of the salt;

a compound of formula (I) which is a stereochemically pure compound, or a salt or hydrate thereof or a hydrate of the salt;

5-amino-7-{3-[(1S,2S)-2-aminocyclopropyl]-1-pyrrolidinyl}-6-fluoro-1-[(1R,2S)-2-fluorocyclopropyl]-8-methyl-1,4-dihydro-4-oxoquinoline-3-carboxylic acid or a salt or hydrate thereof or a hydrate of the salt;

a drug containing any of the above-described compounds, hydrates thereof, salts thereof, and hydrates of the salts as an active ingredient; and an antimicrobial agent containing any of the above-described compounds, hydrates thereof, salts thereof, and hydrates of the salts as an active ingredient.

The present invention also relates to a compound represented by formula (VI) shown below, a salt or hydrate thereof, and a hydrate of the salt:

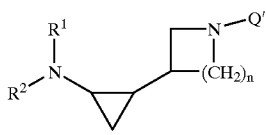
(VI)

wherein $R^1$ and $R^2$ each independently represents a hydrogen atom or an alkyl group having 1 to 6 carbon atoms which may be substituted with one or more substituents selected from the group consisting of a hydroxyl group, a halogen atom, an alkylthio group having 1 to 6 carbon atoms, and an alkyloxy group having 1 to 6 carbon atoms; one of $R^1$ and $R^2$ may be a protective group for amino group; n represents an integer of 1 to 3; Q' represents a hydrogen atom or a protective group for amino group; and the two substituents on the cyclopropane ring,

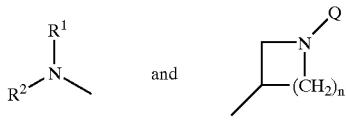

are in a cis-configuration;

a compound of formula (VI), wherein the protective group for amino group is selected from the group consisting of a substituted or unsubstituted alkoxycarbonyl group, a substituted or unsubstituted aralkyloxycarbonyl group, a substituted or unsubstituted acyl group, a substituted or unsubstituted alkyl group, a substituted or unsubstituted aralkyl group, and a substituted silyl group, or a salt or hydrate thereof or a hydrate of the salt;

a compound of formula (VI), wherein the protective group for amino group is selected from the group consisting of a t-butoxycarbonyl group, a 2,2,2-trichloroethoxycarbonyl group, a benzyloxycarbonyl group, a p-methoxylbenzyloxycarbonyl group, a p-nitrobenzyloxycarbonyl group, an acetyl group, a methoxylacetyl group, a trifluoroacetyl group, a chloroacetyl group, a pivaloyl group, a formyl group, a benzoyl group, a t-butyl group, a benzyl group, a p-nitrobenzyl group, a p-methoxybenzyl group, a triphenylmethyl group, a methoxymethyl group, a t-butoxymethyl group, a tetrahydropyranyl group, a 2,2,2-trichloroethoxymethyl group, a trimethylsilyl group, an isopropyldimethylsilyl group, a t-butyldimethylsilyl group, a tribenzylsilyl group, and a t-butyldiphenylsilyl group, or a salt or hydrate thereof or a hydrate of the salt;

a compound of formula (VI), wherein Q' and one of $R^1$ and $R^2$ are different protective groups for amino group, or a salt or hydrate thereof or a hydrate of the salt;

a compound of formula (VI) which is a stereochemically pure compound, or a salt or hydrate thereof or a hydrate of the salt;

and 1-benzyloxycarbonyl-3-[(1S,2S)-2-t-butoxycarbonylamino-cyclopropyl]pyrrolidine or a salt or hydrate thereof or a hydrate of the salt.

The compound according to the present invention, represented by formula (I):

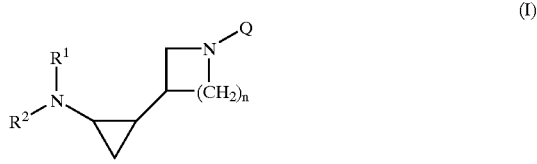
(I)

namely, formula:

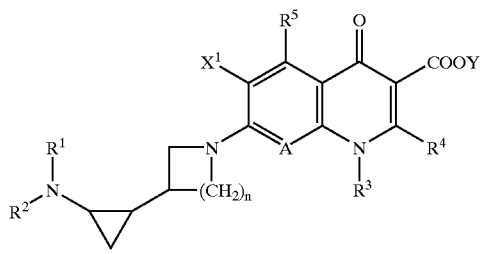

is described with reference to the substituents thereof.

Substituents $R^1$ and $R^2$ each independently represents a hydrogen atom or an alkyl group having 1 to 6 carbon atoms which may be substituted with one or more substituents selected from the group consisting of a hydroxyl group, a halogen atom, an alkylthio group having 1 to 6 carbon atoms, and an alkyloxy group having 1 to 6 carbon atoms.

The alkyl group may be a straight-chain or branched having 1 to 6 carbon atoms and preferably is a methyl group, an ethyl group, an n-propyl group, and an isopropyl group. The hydroxyl-substituted alkyl group having 1 to 6 carbon atoms may be a straight-chain or branched and preferably are a hydroxyethyl group and a hydroxypropyl group.

The alkylthio group having 1 to 6 carbon atoms preferably includes a methylthio group and an ethylthio group. The alkyloxy group having 1 to 6 carbon atoms preferably are a methoxyll group and an ethoxyl group.

Substituent $R^3$ represents an alkyl group having 1 to 6 carbon atoms, an alkenyl group having 2 to 6 carbon atoms, a halogenoalkyl group having 1 to 6 carbon atoms, a substituted or unsubstituted cycloalkyl group having 3 to 6 carbon atoms, a substituted or unsubstituted aryl group, a substituted or unsubstituted heteroaryl group, an alkoxyl group having 1 to 6 carbon atoms, or an alkylamino group having 1 to 6 carbon atoms.

The alkyl group having 1 to 6 carbon atoms preferably are an ethyl group. The alkenyl group having 2 to 6 carbon atoms preferably are a vinyl group or a 1-isopropenyl group.

The halogenoalkyl group having 1 to 6 carbon atoms preferably are a 2-fluoroethyl group. The cycloalkyl group preferably is a cyclopropyl group. The substituent for the cycloalkyl group preferably is a halogen atom, particularly a fluorine atom.

The aryl group which may have a substituent includes a phenyl group and a phenyl group having 1 to 3 substituents selected from the group consisting of a halogen atom (e.g., fluorine, chlorine, and bromine), a lower alkyl group having 1 to 6 carbon atoms, a hydroxyl group, an amino group, a nitro group, a lower alkoxyl group having 1 to 6 carbon atoms, etc., and preferably are a phenyl group, a 2-fluorophenyl group, a 4-fluorophenyl group, 2,4-difluorophenyl group, and a 2-fluoro-4-hydroxyphenyl group.

The heteroaryl group is a substituent derived from an aromatic heterocyclic compound containing at least one hetero atom selected from a nitrogen atom, an oxygen atom and a sulfur atom and includes a pyridyl group and a pyrimidyl group. The substituents on the heteroaryl group preferably are an alkyl group and a halogen atom.

The alkoxyl group having 1 to 6 carbon atoms preferably are a methoxyl group. The alkylamino group having 1 to 6 carbon atoms preferably are a methylamino group.

Substituent $R^3$ is preferably a cycloalkyl group or a halogenocycloalkyl group, still preferably a cyclopropyl group or a 2-halogenocyclopropyl group, in which the halogen atom is preferably a fluorine atom.

Substituent R4 represents a hydrogen atom or an alkylthio group having 1 to 6 carbon atoms, or $R^3$ and $R^4$ may be taken together with part of the mother skeleton (that is, so as to the nitrogen atom to which $R^3$ is bonded and the carbon atom to which $R^4$ is bonded to are involved) to form a cyclic structure. The ring formed may contain a sulfur atom as a ring constituting atom. It may be substituted with an alkyl group having 1 to 6 carbon atoms. The ring can be a 4- to 6-membered ring and may be saturated, partially saturated or unsaturated. The alkylthio group having 1 to 6 carbon atoms preferably are a methylthio group and an ethylthio group.

The condensed ring structure thus formed includes the following structures.

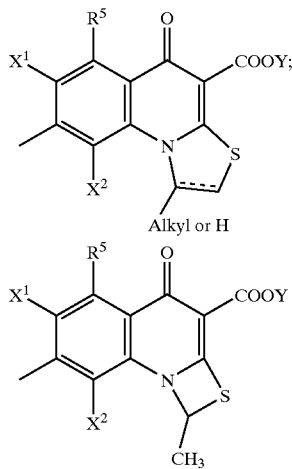

$X^1$ represents a halogen atom or a hydrogen atom.
As for the halogen atom, a fluorine atom is preferable.
$X^1$ preferably is a fluorine atom or a hydrogen atom.

Where A is a partial structure of formula (II):

(II)

$X^2$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms. The amino group may have one or more substituents selected from the group consisting of a formyl group, an alkyl group having 1 to 6 carbon atoms and an acyl group having 2 to 5 carbon atoms.

The alkyl group may be a straight-chain or branched having 1 to 6 carbon atoms and preferably are a methyl group, an ethyl group, an n-propyl group, and an isopropyl group. The alkenyl group may be a straight-chain or branched having 2 to 6 carbon atoms and preferably is a vinyl group. The alkynyl group may be a straight-chain or branched having 2 to 6 carbon atoms and preferably is an ethynyl group. The halogenomethyl group may contain 1 to 3 halogen atoms, and the halogen atom thereof is preferably a fluorine atom. The alkoxyl group may be those having 1 to 6 carbon atoms and preferably is a methoxyl group. The halogenomethoxyl group may have 1 to 3 halogen atoms, and the halogen atom thereof is preferably a fluorine atom.

$R^3$ and $X^2$ may be taken together with part of the mother skeleton (that is, so as to the nitrogen atom to which $R^3$ is bonded and the carbon atom to which $x^2$ is bonded are involved) to form a cyclic structure that may contain an oxygen atom, a nitrogen atom or a sulfur atom as a ring constituting atom and/or may be substituted with an alkyl group having 1 to 6 carbon atoms. The cyclic structure can be a 4- to 7-membered ring and may be saturated, partially saturated or unsaturated.

The condensed ring structure thus formed includes the following structures.

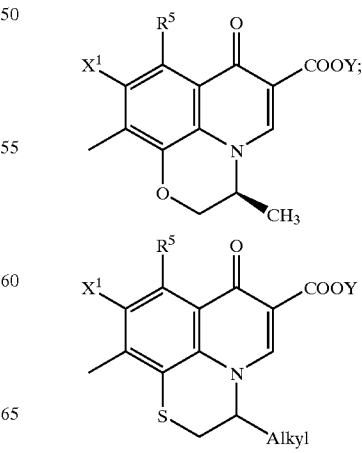

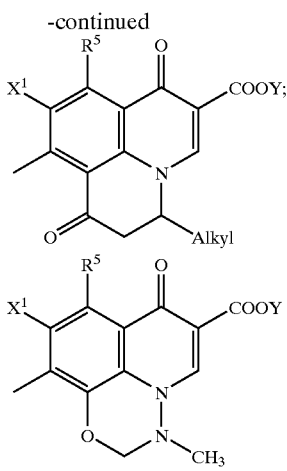

A 6-carboxy-2,3-dihydro-3-(S)-methyl-7-oxo-7H-pyrido[1,2,3-de][1,4]benzoxazin-10-yl group is particularly preferred of them.

Substituent $R^5$ represents a hydrogen atom, an amino group, a hydroxyl group, a thiol group, a halogenomethyl group, an alkyl group having 1 to 6 carbon atoms, an alkenyl group having 2 to 6 carbon atoms, -an alkynyl group having 2 to 6 carbon atoms or an alkoxyl group having 1 to 6 carbon atoms, in which the amino group may be substituted with one or more substituents selected from the group consisting of a formyl group, an alkyl group having 1 to 6 carbon atoms, and an acyl group having 2 to 5 carbon atoms.

The alkyl group can be a straight-chain or branched having 1 to 6 carbon atoms and preferably is a methyl group, an ethyl group, an n-propyl group, and an isopropyl group. The alkenyl group can be a straight-chain or branched having 2 to 6 carbon atoms and preferably is a vinyl group. The alkynyl group may be a straight-chain or branched having 2 to 6 carbon atoms and preferably is an ethynyl group. The halogenomethyl group may contain 1 to 3 halogen atoms, and the halogen atom thereof preferably is a fluorine atom. The alkoxyl group can be those having 1 to 6 carbon atoms and preferably is a methoxyl group.

The acyl group having 2 to 5 carbon atoms which may be a substitutent for the amino group preferably are an acetyl group, a propanoly group and a butanoyl group.

Where $X^2$ or $R^5$ is an amino group, a hydroxyl group or a thiol group, these groups may be protected by commonly used protective groups, such as a substituted or unsubstituted alkoxycarbonyl group, a substituted or unsubstituted aralkyloxycarbonyl group, a substituted or unsubstituted acyl group, a substituted or unsubstituted alkyl group, a substituted or unsubstituted aralkyl group, and a silyl group substituted with an alkyl group or an aralkyl group (they may be the same or different).

Specific examples of the protective group include substituted or unsubstituted alkoxycarbonyl groups, e.g., a t-butoxycarbonyl group and a 2,2,2-trichloroethoxycarbonyl group; substituted or unsubstituted aralkyloxycarbonyl groups, e.g., a benzyloxycarbonyl group, a p-methoxybenzyloxycarbonyl group, and a p-nitrobenzyloxycarbonyl group; substituted or unsubstituted acyl groups, e.g., an acetyl group , a methoxyacetyl group, a trifluoroacetyl group, a chloroacetyl group, a pivaloyl group, a formyl group, and a benzoyl group; substituted or unsubstituted alkyl or aralkyl groups, e.g., a t-butyl group, a benzyl group, a p-nitrobenzyl group, a p-methoxybenzyl group, a triphenylmethyl group, and a phenethyl group; ether groups, e.g, a methoxymethyl group, a t-butoxymethyl group, a tetrahydropyranyl group, and a 2,2,2-trichloroethoxymethyl group; and substituted silyl groups, e.g., a trimethylsilyl group, an isopropyldimethylsilyl group, a t-butyldimethylsilyl group, a tribenzylsilyl group, and a t-butyldiphenylsilyl group. The compounds whose substituents are protected by these protective groups are particularly useful as an intermediate for preparing the compounds of formula (I).

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group having 1 to 6 carbon atoms in the alkyl moiety thereof.

The alkyl group having 1 to 6 carbon atoms preferably are a methyl group, an ethyl group, a propyl group, an isopropyl group, a butyl group and a t-butyl group. The alkoxymethyl group having 2 to 7 carbon atoms preferably are a methoxymethyl group and an ethoxymethyl. The phenylalkyl group having 1 to 6 carbon atoms in the alkyl moiety thereof preferably are a benzyl group and a phenetyl group.

Where A is a partial structure represented by formula (II), a preferable combination of substituents $R^5$ and $X^2$ is that $R^5$ is selected from an amino group, a hydrogen atom, a hydroxyl group, and an alkyl group having 1 to 6 carbon atoms, and $X^2$ is selected from an alkyl group having 1 to 6 carbon atoms, an alkoxyl group having 1 to 6 carbon atoms, a halogenomethoxyl group, and a hydrogen atom. In a still preferred combination, $R^5$ is an amino group, a hydrogen atom, a hydroxyl group or a methyl group, and $X^2$ is a methyl group, a methoxyl group, a difluoromethoxyl group or a hydrogen atom.

In the above case, $X^1$ preferably is a fluorine atom with respect to $R^5$ and $X^2$. Where $X^1$ and $X^2$ are both a halogen atom, $X^1$ preferably is a fluorine atom, and $X^2$ preferably is a fluorine atom or a chlorine atom.

The compounds according to the present invention are characterized in that the quinolone skeleton has a substituent represented by formula:

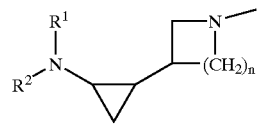

at the 7-position or a corresponding position, namely, the formula that the amino group or alkylamino group:

and a 4-membered (n=1) to 6-membered (n=3) nitrogen-containing saturated heterocyclic substituent:

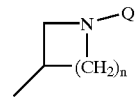

are bonded to the cyclopropyl group.

While the amino moiety and the nitrogen-containing saturated heterocyclic moiety can be in a cis- or trans-configuration with respect to the cyclopropyl group (cyclopropane ring), a cis-configuration shown below is preferred.

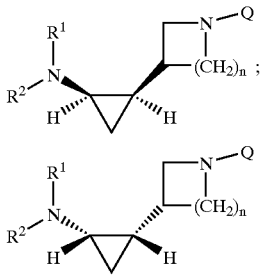

Where n is 2 or 3, the nitrogen-containing saturated heterocyclic moiety and the cyclopropane ring are bonded in two modes to provide isomers. Such isomers are illustrated below, taking the structure wherein n=2 for instance. Similar isomers are produced when n is 3. The present invention is intended to embrace all these isomers under the scope thereof.

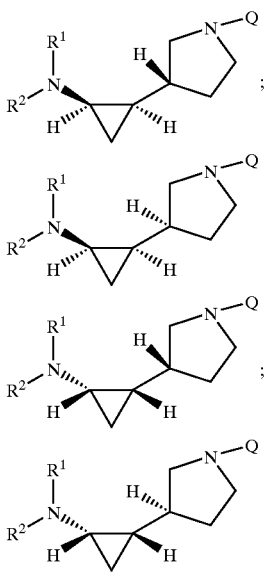

The cyclopropyl moiety may have further substituents, for example, a fluorine atom, a methyl group, an ethyl group, a trifluoromethyl group, etc.

The halogenocyclopropyl group as $R^3$ is then described. The substituent halogen atom includes a fluorine atom and a chlorine atom, with a fluorine atom being preferred.

It is particularly preferred that the substituent halogen atom and the pyridonecarboxylic acid moiety be in a cis-configuration with respect to the cyclopropane ring.

Regardless of stereoisomerism of the 7-positioned substituent, the cis-2-halogenocyclopropyl moiety of $R^3$ makes a pair of antipodes, each of which was observed to exhibit potent antimicrobial activity and high safety.

Where the compound of formula (I) has such a structure that produces diastereomers, it is desirable to administer a compound comprising a pure diastereomer in administration to humans or animals. The language "a compound comprising a pure diastereomer" as used herein is construed as including not only a compound containing no other diastereomer at all but a compound containing other diastereomers to such an extent that the compound is recognized to be stereochemically pure as a whole. In other words, it is construed as meaning that other diastereomers may exist to some extent as long as the existence gives no substantial influence on physiological activities or physicochemical constants.

The language "stereochemically pure" as used herein is intended to mean that a compound comprises only one of its stereoisomers ascribed to its asymmetric carbon atom. The latitude of the term "pure" in "pure diastereomer" also applies here.

The pyridonecarboxylic acid derivative of the present invention may present in either a free form or a form of an acid addition salt or a carboxylic acid salt. Acid addition salts include inorganic acid salts, such as a hydrochloride, a sulfate, a nitrate, a hydrobromide, a hydroiodide, and a phosphate; and organic acid salts, such as an acetate, a metanesulfonate, a benzenesulfonate, a toluenesulfonate, a citrate, a maleate, a fumarate, and a lactate.

The carboxylic acid salts include inorganic salts and organic salts, such as alkali metal salts, e.g., a lithium salt, a sodium salt, and a potassium salt; alkaline earth metal salts, e.g., a magnesium salt and a calcium salt; an ammonium salt; a triethylamine salt, an N-methylglucamine salt, and a tris-(hydroxymethyl)aminomethane salt.

The free pyridonecarboxylic acid derivatives, acid addition salts thereof, and carboxylic acid salts thereof may be present as a hydrate.

On the other hand, quinolone derivatives with the carboxylic acid moiety thereof having an ester form are useful as an intermediate for synthesis or a pro-drug. For example, alkyl esters, benzyl esters, alkoxylalkyl esters, phenylalkyl esters, and phenyl esters are useful as synthetic intermediates.

Esters which can be used as pro-drugs are those which are susceptible to an in vivo cleavage to form a free carboxylic acid, including an acetoxymethyl ester, a pivaloyloxymethyl ester, an ethoxycarbonyl ester, a choline ester, a dimethylaminoethyl ester, a 5-indanyl ester, a phthalidinyl ester, a 5-alkyl-2-oxo-1,3-dioxol-4-ylmethyl ester, and oxoalkyl esters, such as a 3-acetoxy-2-oxobutyl ester.

The compound of formula (I) can be prepared through various processes. A preferred process comprises reacting a compound represented by formula (III):

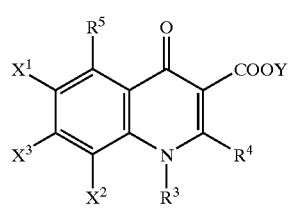

(III)

wherein $X^3$ represents a leaving group, such as a fluorine atom, a chlorine atom, a bromine atom, an alkylsulfonyl group having 1 to 3 carbon atoms, or an arylsulfonyl group, e.g., a benzenesulfonyl group or a toluenesulfonyl group; Y has the same meaning as in formula (I) or represents a boron-containing group represented by formula (IV):

 (IV)

wherein $R^6$ and $R^7$ each represents a fluorine atom or a lower alkylcarbonyloxy group;

and $R^3$, $R^4$, $R^5$, $X^1$, and $X^2$ are as defined in formula (I), with a compound represented by formula (V):

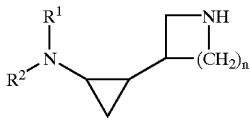

(V)

wherein $R^1$, $R^2$, and n are as defined in formula (I), except that $R^1$ may be a nitrogen-protective group Rx.

Any protective group generally used in the art can be used as protective group Rx. Examples of useful protective groups include alkoxylcarbonyl groups, e.g., a t-butoxycarbonyl group and a 2,2,2-trichloroethoxycarbonyl group; aralkyloxycarbonyl groups, e.g., a benzyloxycarbonyl group, a p-methoxybenzyloxycarbonyl group, and a p-nitrobenzyloxycarbonyl group; acyl groups, e.g., an acetyl group, a methoxyacetyl group, a trifluoroacetyl group, a chloroacetyl group, a pivaloyl group, a formyl group, and a benzoyl group; alkyl or aralkyl groups, e.g., a t-butyl group, a benzyl group, a p-nitrobenzyl group, a p-methoxybenzyl group, and a triphenylmethyl group; ether groups, e.g, a methoxymethyl group, a t-butoxymethyl group, a tetrahydropyranyl group, and a 2,2,2-trichloroethoxymethyl group; and substituted silyl groups, e.g., a trimethylsilyl group, an isopropyldimethylsilyl group, a t-butyldimethylsilyl group, a tribenzylsilyl group, and a t-butyldiphenylsilyl group, or an acid addition salt thereof.

The resulting compound in which Y is an alkyl group having 1 to 6 carbon atoms, an alkoxymethyl group having 2 to 7 carbon atoms or a phenylalkyl group having 1 to 6 carbon atoms in the alkyl moiety thereof can be converted to the corresponding carboxylic acid by hydrolysis under an acidic or basic condition commonly used for hydrolysis of carboxylic acid esters. The protective group, if any, is removed under properly selected conditions to obtain a desired compound (I).

The compound obtained by the substitution reaction between the compound (III) wherein Y is the group (IV) and the compound (V) can be converted to the corresponding carboxylic acid by treatment with an acidic or basic compound.

The substitution reaction between the compound of formula (III) and the compound of formula (V) is carried out with or without a solvent. The solvent, if used, is not limited as long as it is inert under the reaction conditions. Suitable solvents include dimethyl sulfoxide, pyridine, acetonitrile, ethanol, chloroform, dimethylformamide, dimethylacetamide, N-methylpyrrolidone, tetrahydrofuran, water, and 3-methoxybutanol. These solvents may be used as a mixture thereof.

The reaction is usually performed at room temperature to 200° C., preferably 25 to 150° C., for 0.5 to 48 hours. The reaction usually completes in about 0.5 to 2 hours. It is advantageous to conduct the reaction in the presence of an acid acceptor, such as an inorganic base (e.g., an alkali metal or alkaline earth metal carbonate or hydrogencarbonate) or an organic base (e.g., triethylamine, pyridine or 1,8-diazabicycloundecene).

The compound of formula (V) can be prepared by various processes. A preferred process is shown in Reference Examples hereinafter given, but the process is not limited thereto. Most generally, the compound of formula (V) is prepared by removing the protective group from a compound represented by formula (VI) shown below, in which the nitrogen atom is protected by a protective group Q'.

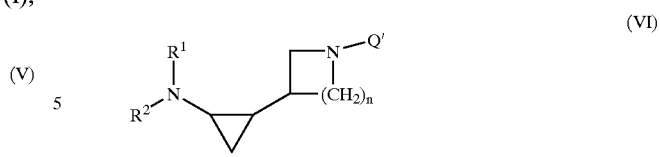

(VI)

wherein $R^1$ and $R^2$ each represent a hydrogen atom or an alkyl group having 1 to 6 carbon atoms, which may have one or more substituents selected from the group consisting of a hydroxyl group, a halogen atom, an alkylthio group having 1 to 6 carbon atoms, and an alkyloxy group having 1 to 6 carbon atoms; one of $R^1$ and $R^2$ may be an protective group for amino group; n represents an integer of 1 to 3; Q' represents a protective group for amino group; and the two substituents on the cyclopropane ring,

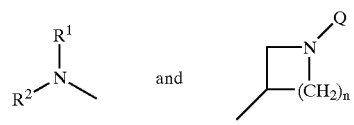

are in a cis-configuration.

The compound (VI) may exist in the form of a salt, a hydrate, or a hydrate of the salt. Acid addition salts include inorganic acid salts and organic acid salts. Examples of the inorganic acid salts are a hydrochloride, a sulfate, a nitrate, a hydrobromide, a hydroiodide, and a phosphate. Examples of the organic acid salts include sulfonates, such as a metanesulfonate, a benzenesulfonate, and a toluenesulfonate, and carboxylates, such as an acetate, a citrate, a maleate, a fumarate, and a lactate.

Where Q' and one of $R^1$ and $R^2$ both represent an protective group for amino group, while they may be the same or different, it is advantageous for the preparation of the compound (I) that these protective groups are different so that they are cleaved under the respective different reaction conditions.

The protective group for amino group as $R^1$ or $R^2$ and Q' includes substituted or unsubstituted alkoxycarbonyl groups, e.g., a t-butoxycarbonyl group and a 2,2,2-trichloroethoxycarbonyl group; substituted or unsubstituted aralkyloxycarbonyl groups, e.g., a benzyloxycarbonyl group, a p-methoxybenzyloxycarbonyl group, and a p-nitrobenzyloxycarbonyl group; substituted or unsubstituted acyl groups, e.g., an acetyl group, a methoxyacetyl group, a trifluoroacetyl group, a chloroacetyl group, a pivaloyl group, a formyl group, and a benzoyl group; substituted or unsubstituted alkyl or aralkyl groups, e.g., a t-butyl group, a benzyl group, a p-nitrobenzyl group, a p-methoxybenzyl group, and a triphenylmethyl group; ether groups, e.g., a methoxymethyl group, a t-butoxymethyl group, a tetrahydropyranyl group, and a 2,2,2-trichloroethoxymethyl group; and substituted silyl groups, e.g., a trimethylsilyl group, an isopropyldimethylsilyl group, a t-butyldimethylsilyl group, a tribenzylsilyl group, and a t-butyldiphenylsilyl group.

Cis-2-fluorocyclopropylamine comprising a pure isomer, which is preferred for the synthesis of the compound of formula (I) comprising a pure isomer, can be synthesized by, for example, the process described in JP-A-2-231475 (the term "JP-A" as used herein means an "unexamined published Japanese patent application"). Synthesis of the compound of formula (I) comprising a pure isomer from the resulting optically active cis-2-fluorocyclopropylamine derivative can be carried out by, for example, the process described in JP-A-2-231475.

The compounds of the present invention have potent antimicrobial activity and are therefore useful as drugs for humans, animals or fishes, agricultural chemicals, or food preservatives.

For use as drugs for humans, the dose of the compound is in the range of from 50 mg to 1 g, and preferably from 100 mg to 300 mg, per day for an adult.

For veterinary use, the dose is generally in the range of from 1 to 200 mg, and preferably from 5 to 100 mg, per kg of body weight per day while varying depending on the purpose of administration (for therapy or for prevention), the kind and the size of the animal, the kind of the pathogenic organisms, and severity of symptom.

The above-mentioned daily dose is given once a day or in 2 to 4 divided doses. If necessary, a daily dose may exceed the above-specified range.

The compounds according to the present invention are active on a broad range of microorganisms causing various infectious diseases and effective to prevent, alleviate or cure diseases caused by these pathogens.

Examples of bacteria or bacterium-like microorganisms on which the compounds of the invention are effective include staphylococci, *Streptococcus pyogenes, Streptococcus haemolyticus, Streptococcus faecalis, Streptococcus pneumoniae*, peptostreptococci, *Neisseria gonorrhoeae, Escherichia coli*, Citrobacter sp., Shigella sp., *Klebsiella pneumoniae*, Enterobacter sp., Serratia sp., Proteus sp., *Pseudomonas aeruginosa, Haemophilus influenzae*, Acinetobacter sp., Campylobacter sp., and *Chlamydozoon trachomatis*.

Diseases which are caused by these pathogens include folliculitis, furuncle, carbuncle, erysipelas, phlegmon, lymphangitis/lymphadenitis, felon, subcutaneous abscess, spiradenitis, acne agminata, infectious atheroma, perianal abscess, mastadenitis, superficial secondary infections after trauma, burn or surgery trauma, pharyngolaryngitis, acute bronchitis, tonsillitis, chronic bronchitis, bronchiectasis, diffuse panbronchiolitis, secondary infections of chronic respiratory diseases, pneumonia, pyelonephritis, cystitis, prostatitis, epididymitis, gonococcal urethritis, non-gonococcal urethritis, cholecystitis, cholangitis, bacillary dysentery, enteritis, adnexitis, intrauterine infections, bartholinitis, blepharitis, hordeolum, dacryocystitis, tarsadenitis, keratohelcosis, otitis media, sinusitis, paradentosis, pericoronitis, gnathitis, peritonitis, endocarditis, septicemia, meningitis, and skin infections.

The compounds of the present invention are also effective on various microorganisms causing veterinary diseases, such as those belonging to the genera Escherichia, Salmonella, Pasteurella, Haemophilus, Bordetella, Staphylococcus, and Mycoplasma. Illustrative examples of the veterinary diseases include those of fowl, such as colibacillosis, pullorum disease, avian paratyphosis, fowl cholera, infectious coryza, staphylomycosis, and mycoplasmosis; those of pigs, such as colibacillosis, salmonellosis, pasteurellosis, hemophilus infections, atrophic rhinitis, exudative epidermitis, and mycoplasmosis; those of cattle, such as colibacillosis, salmonellosis, hemorrhagic septicemia, mycoplasmosis, bovine contagious pleuropneumonia, and bovine mastitis; those of dogs, such as colisepsis, salmonellosis, hemorrhagic septicemia, pyometra, and cystitis; those of cats, such as exudative pleurisy, cystitis, chronic rhinitis, and hemophilus infections; and those of kittens, such as bacterial diarrhea and mycoplasmosis.

Dosage forms of pharmaceutical preparations containing the compound of the present invention are appropriately selected according to the administration route and can be prepared by conventional preparation methods. Examples of dosage forms for oral administration include tablets, powders, granules, capsules, solutions, syrups, elixirs, and oily or aqueous suspensions.

Injectable preparations may contain adjuvants, such as stabilizers, antiseptics, and solubilizers. The injectable solution which may contain these adjuvants may be put into a container and solidified by, for example, lyophilization to prepare a solid preparation which is dissolved on use. The container may contain either a single dose or multiple doses.

Preparations for external application include solutions, suspensions, emulsions, ointments, gels, creams, lotions, and sprays.

Solid preparations may contain, in addition to the active compound, pharmaceutically acceptable additives. For example, the active compound is mixed with additives selected according to necessity from among fillers, extenders, binders, disintegrators, absorption accelerators, wetting agents, and lubricants and formulated into solid preparations.

Liquid preparations include solutions, suspensions, and emulsions. They may contain adjuvants, such as suspending agents, emulsifiers, and so forth.

The compound can be administered to animals orally either directly or by mixing with feedstuff, or in a dissolved form directly given to animals or by mixing with water or feedstuff or non-orally by injection.

For veterinary use, the compound can be formulated into powders, fine granules, soluble powders, syrups, solutions, and injections according to the customary methods in the art.

Formulation Examples are shown below.

Formulation Example 1

Capsules

| | |
|---|---|
| Compound of Example 2 | 100.0 mg |
| Corn starch | 23.0 mg |
| CMC.Ca | 22.5 mg |
| Hydroxymethyl cellulose | 3.0 mg |
| Magnesium stearate | 1.5 mg |
| Total: | 150 mg |

Formulation Example 2

Solution

| | |
|---|---|
| Compound of Example 2 | 1 to 10 g |
| Acetic acid or sodium hydroxide | 0.5 to 2 g |
| Ethyl p-hydroxybenzoate | 0.1 g |
| Purified water | 87.9 to 98.4 g |
| Total: | 100 g |

Formulation Example 3

Powder for Mixing with Feed

| | |
|---|---|
| Compound of Example 2 | 1 to 10 g |
| Corn starch | 89.5 to 98.5 g |
| Light anhydrous silicic acid | 0.5 g |
| Total: | 100 g |

BEST MODE OF CARRYING OUT THE INVENTION

The present invention will further be illustrated in greater detail by way of Examples and Reference Examples, but the present invention should not be construed as being limited thereto. The antimicrobial activity of the compounds prepared was examined in accordance with the standard method specified by the Japan Chemotherapeutic Society, and the results obtained were expressed in terms of minimum inhibitory concentration (MIC; μg/ml).

Example 1

5-Amino-7-[3-(1,2-cis-2-aminocyclopropyl)-1-pyrrolidinyl]-6-fluoro-1-[(1R,2S)-2-fluorocyclopropyl]-8-methyl-1,4-dihydro-4-oxoquinoline-3-carboxylic Acid (Isomer A)

Triethylamine (2.5 ml) was added to a solution of 316.1 mg (1.01 mmol) of 5-amino-6,7-difluoro-l-[(1R,2S)-2-fluorocyclopropyl]-8-methyl-1,4-dihydro-4-oxoquinoline-3-carboxylic acid and 343.6 mg (1.52 mmol) of 1-benzyloxycarbonyl-3-(cis-2-t-butoxycarbonylaminocyclopropyl)pyrrolidine (isomer A) in 5 ml of dimethyl sulfoxide, and the mixture was heated under reflux at 130° C. for 4 days. The solvent was removed by evaporation under reduced pressure, and chloroform was added to the residue, followed by washing successively with a 10% citric acid aqueous solution and a saturated sodium chloride aqueous solution. The organic layer was dried over anhydrous sodium sulfate, and the solvent was evaporated under reduced pressure. To the residue was added 10 ml of concentrated hydrochloric acid under cooling with ice. After stirring at room temperature for 30 minutes, water was added to the reaction mixture, followed by extraction with dichloromethane. The aqueous layer was neutralized with 5N and 1N sodium hydroxide aqueous solutions and extracted with chloroform. The organic layer was dried over anhydrous sodium sulfate, and the solvent was evaporated under reduced pressure. The residue was recrystallized from ethanol and diethyl ether to give 122.8 mg (29.0%) of the title compound (isomer A) as yellow crystals.

$^1$H-NMR (0.1N-NaOD) δ ppm:
0.00–0.10 (1H, m), 0.55–0.75 (2H, m), 1.00–1.15 (1H, m), 1.35–1.50 (1H, m), 1.55–1.80 (1H, m), 1.85–2.00 (1H, m), 2.00–2.15 (1H, m), 2.15–2.30 (4H, m), 3.10–3.70 (4H, m), 3.80–3.90 (1H, m), 4.60–5.00 (1H, m), and 8.18 and 8.20 (1H, d each, J=2.9, 2.4 Hz each).

Elementary Analysis for $C_{21}H_{24}F_2N_4O_3$: Calcd. (%): C, 60.28; H, 5.78; N, 13.39. Found (%): C, 60.09; H, 5.96; N, 13.06.

Example 2

5-Amino-7-[3-(1,2-cis-2-aminocyclopropyl)-1-pyrrolidinyl]-6-fluoro-1-[(1R,2S)-2-fluorocyclopropyl]-8-methyl-1,4-dihydro-4-oxoquinoline-3-carboxylic Acid (Isomer B)

Triethylamine (2 ml) was added to a solution of 195.9 mg (0.63 mmol) of 5-amino-6,7-difluoro-1-[(1R,2S)-2-fluorocyclopropyl]-8-methyl-1,4-dihydro-4-oxoquinoline-3-carboxylic acid and 213.0 mg (0.94 mmol) of 1-benzyloxy-carbonyl-3-(cis-2-t-butoxycarbonylaminocyclopropyl)pyrrolidine (isomer B) in 4 ml of dimethyl sulfoxide, and the mixture was heated under reflux at 130° C. for 45 hours. The solvent was removed by evaporation under reduced pressure, and chloroform was added to the residue, followed by washing successively with a 10% citric acid aqueous solution and a saturated sodium chloride aqueous solution. The organic layer was dried over anhydrous sodium sulfate, and the solvent was evaporated under reduced pressure. To the residue was added 10 ml of concentrated hydrochloric acid under cooling with ice. After stirring at room temperature for 30 minutes, water was added to the reaction mixture, followed by extraction with dichloromethane. The aqueous layer was neutralized with 5N and 1N sodium hydroxide aqueous solutions and extracted with chloroform. The aqueous layer was adjusted to a pH of 10 or higher with a 5N sodium hydroxide aqueous solution and extracted with chloroform. The aqueous layer was neutralized with concentrated hydrochloric acid and 1N hydrochloric acid and extracted with chloroform. The organic layer was dried over anhydrous sodium sulfate, and the solvent was evaporated under reduced pressure. The residue was recrystallized from ethanol and diethyl ether to give 65.9 mg (25.1%) of the title compound (isomer B) as yellow crystals.

1H-NMR (0.1N-NaOD) δ ppm: 0.00–0.10 (1H, m), 0.55–0.70 (2H, m), 0.95–1.15 (1H, m), 1.30–1.50 (1H, m), 1.60–1.80 (1H, m), 1.80–2.10 (2H, m), 2.10–2.25 (4H, m), 3.00–3.70 (4H, m), 3.75–3.85 (1H, m), 4.65–4.95 (1H, m), and 8.13 and 8.14 (1H, d each, J=2.9, 2.0 Hz each).

Elementary Analysis for $C_{21}H_{24}F_2N_4O_3 \cdot 0.5H_2O$: Calcd. (%): C, 59.01; H, 5.90; N, 13.11. Found (%): C, 59.10; H, 5.66; N, 13.06.

Example 3

5-Amino-7-{3-[(1S,2S)-2-aminocyclopropyl]-1-pyrrolidinyl}-6-fluoro-1-[(1R,2S)-2-fluorocyclopropyl]-8-methyl-1,4-dihydro-4-oxoquinoline-3-carboxylic Acid (Isomer B$^1$)

Triethylamine (4 ml) was added to a solution of 526.3 mg (1.69 mmol) of 5-amino-6,7-difluoro-1-[(1R,2S)-2-fluorocyclopropyl]-8-methyl-1,4-dihydro-4-oxoquinoline-3-carboxylic acid and 572.2 mg (2.53 mmol) of 1-benzyloxycarbonyl-3-[(1S,2S)-2-t-butoxycarbonylaminocyclopropyl]pyrrolidine (isomer B) in 8 ml of dimethyl sulfoxide, and the mixture was heated under reflux at 130° C. for 90 hours. The solvent was removed by evaporation under reduced pressure, and chloroform was added to the residue, followed by washing with a 10% citric acid aqueous solution and a saturated sodium chloride aqueous solution. The organic layer was dried over anhydrous sodium sulfate, and the solvent was evaporated under reduced pressure. The residue was purified by silica gel column chromatography (chloroform:methanol=9:1) to obtain 551.4 mg of a protected compound and 141.4 mg of a mixture of the protected compound and by-products as a brown caramel-like substance.

To the resulting protected compound (551.4 mg) was added 10 ml of concentrated hydrochloric acid under ice-cooling, followed by stirring at room temperature for 20 minutes. Water was added to the reaction mixture, and the mixture was extracted with dichloromethane. The aqueous layer was neutralized with 5N and 1N sodium hydroxide aqueous solutions and extracted with chloroform. The organic layer was removed by evaporation, and the residue was adjusted to a pH of 10 or higher with water and a 1N sodium hydroxide aqueous solution and extracted with chloroform. The aqueous layer was neutralized with concentrated hydrochloric acid and 1N hydrochloric acid and extracted with chloroform. The first aqueous layer was adjusted to a pH of 10 or higher with a 5N sodium hydroxide aqueous solution and extracted with chloroform. The aqueous layer was neutralized with concentrated hydrochloric acid and 1N hydrochloric acid and extracted with chloroform. The combined organic layer was dried over anhydrous sodium sulfate, and the solvent was evaporated under reduced pressure to obtain 286.1 mg of a crude carboxylic acid.

The mixture (141.4 mg) of the protected compound and by-products was similarly treated to obtain 62.3 mg of a crude carboxylic acid.

Recrystallization of the resulting crude carboxylic acid from ethanol gave 204.4 mg (29.0%) of the title compound as yellow crystals.

$^1$H-NMR (0.1N-NaOD) δ ppm: −0.05–0.05 (1H, m), 0.55–0.65 (2H, m), 0.90–1.10 (1H, m), 1.30–1.40 (1H, m), 1.60–1.70 (1H, m), 1.80–1.90 (1H, m), 2.00–2.10 (1H, m), 2.10–2.20 (4H, m), 3.20–3.30 (1H, m), 3.30–3.40 (2H, m), 3.50–3.60 (1H, m), 3.70–3.80 (1H, m), 4.70–4.95 (1H, m), and 8.11 (1H, brs).

Elementary Analysis for $C_{21}H_{24}F_2N_4O_3$: Calcd. (%): C, 60.28; H, 5.78; N, 13.39 Found (%): C, 60.21; H, 5.72; N, 13.15

Melting Point: 193–196° C.

Reference Example A

Cis-2-methoxycarbonylcyclopronanecarboxylic Acid

To 150 ml of a methanol solution of 14.68 g (92.8 mmol) of dimethyl cis-1,2-cyclopropanedicarboxylate was added 67 ml of an aqueous solution of 7.52 g (113.9 mmol) of potassium hydroxide under cooling with ice, and the mixture was stirred at room temperature for 24 hours. After completion of the reaction, the solvent was removed by evaporation under reduced pressure, and to the residue was added water. The reaction mixture was washed with diethyl ether. The aqueous layer was adjusted to pH 2 with concentrated hydrochloric acid and extracted with ethyl acetate. The organic layer was dried over anhydrous sodium sulfate, and the solvent was evaporated under reduced pressure to give 12.38 g (92.5%) of the title compound as a colorless oily substance.

$^1$H-NMR (CDCl$_3$) δ ppm: 1.35 (1H, dt, J=8.3, 4.9 Hz), 1.70 (1H, dt, J=6.8, 4.9 Hz), 2.05–2.20 (2H, m), and 3.72 (3H, m).

Reference Example B t-Butyl Cis-2-methoxycarbonylcyclopropanecarboxylate

To 70 ml of an anhydrous tetrahydrofuran solution of 6.83 g (47.4 mmol) of cis-2-methoxycarbonylcyclopropanecarboxylic acid were added 1.16 g (9.48 mmol) of dimethylaminopyridine and 13.45 g (61.6 mmol) of di-t-butyl dicarbonate at room temperature, and the mixture was stirred at the same temperature for 4 hours. After completion of the reaction, the solvent was removed by evaporation under reduced pressure, and ethyl acetate was added to the residue. The mixture was washed successively with 0.5N hydrochloric acid, water, and a saturated sodium chloride aqueous solution. The organic layer was dried over anhydrous sodium sulfate, and the solvent was evaporated under reduced pressure to give 9.49 g (quantitative) of the title compound as a brown oily substance. $^1$H-NMR (CDCl$_3$) δ ppm: 1.10–1.20 (1H, m), 1.44 (9H, s), 1.55–1.65 (1H, m), 1.95–2.05 (2H, m), and 3.67 (3H, s).

Reference Example C

Cis-2-t-butoxycarbonylcyclopropanecarboxylic Acid

To 100 ml of a methanol solution of 9.49 g (47.4 mmol) of t-butyl cis-2-methoxycarbonylcyclopropanecarboxylate was added 40 ml of an aqueous solution of 4.06 g (61.5 mmol) of potassium hydroxide under cooling with ice, followed by stirring at room temperature for 24 hours. After completion of the reaction, the solvent was evaporated under reduced pressure. Water was added to the residue, and the mixture was washed with diethyl ether. The aqueous layer was adjusted to a pH of 2 to 3 with concentrated hydrochloric acid and extracted with ethyl acetate. The organic layer was dried over anhydrous sodium sulfate, and the solvent was evaporated under reduced pressure to give 7.56 g (85.7%) of the title compound as a pale yellow solid.

$^1$H-NMR (CDCl$_3$) δ ppm: 1.30–1.40 (1H, m), 1.45 (9H, s), 1.60–1.65 (1H, m), and 2.00–2.10 (2H, m)

Reference Example D

Ethyl 3-(Cis-2-t-butoxycarbonylcyclopropyl)-3-oxopropionate

To 100 ml of an anhydrous tetrahydrofuran solution of 7.56 g (40.6 mmol) of cis-2-t-butoxycarbonylcyclopropanecarboxylic acid was added 7.57 g (46.7 mmol) of 1,1-carbonyldiimidazole under cooling with ice. After stirring the mixture was stirred at room temperature for 2 hours, the solvent was evaporated under reduced pressure. To 50 ml of an anhydrous tetrahydrofuran solution of the resulting residue was added 80 ml of an anhydrous tetrahydrofuran solution of 101.5 mmol of previously prepared magnesium monoethyl malonate was added, followed by stirring overnight. After completion of the reaction, the solvent was removed by evaporation under reduced pressure, and ethyl acetate was added to the residue. The mixture was washed successively with 0.5N hydrochloric acid, a saturated sodium hydrogencarbonate aqueous solution, and a saturated sodium chloride aqueous solution. The organic layer was dried over anhydrous sodium sulfate, and the solvent was evaporated under reduced pressure. The residue was purified by silica gel column chromatography (hexane:ethyl acetate=7:3) to give 6.67 g (64.1%) of the titled compound as a yellow oily substance.

$^1$H-NMR (CDCl$_3$) δ ppm: 1.20 (1H, dt, J=7.8, 4.9 Hz), 1.29 (3H, t, J=7.3 Hz), 1.42 (9H, s), 1.71 (1H, dt, J=6.8, 4.9 Hz), 2.00–2.10 (1H, m), 2.30–2.40 (1H, m), 3.55 (1H, d, J=15.6 Hz), 3.57 (1H, d, J=15.6 Hz), 4.20 (2H, q, J=7.3 Hz).

Reference Example E

Ethyl 3-(Cis-2-t-butoxycarbonylcyclopropyl)acrylate

To 70 ml of a methanol solution of 6.67 g (26.0 mmol) of ethyl 3-(cis-2-t-butoxycarbonylcyclopropyl)-3-oxopropionate was added 492.2 mg (13.0 mmol) of sodium borohydride at −10° C., and the mixture was stirred at that temperature for 20 minutes. A saturated ammonium chloride aqueous solution was added thereto, and the reaction mixture was extracted with chloroform. The organic layer was dried over anhydrous sodium sulfate, and the solvent was evaporated under reduced pressure to obtain 6.52 g (97.0%) of a crude alcohol as a colorless oily substance.

To 150 ml of a dichloromethane solution of the crude alcohol (6.52 g, 25.2 mmol) were added 7.04 ml (50.4 mmol) of triethylamine and 2.54 ml (32.8 mmol) of methanesulfonyl chloride while cooling with ice. After the mixture was stirred at the same temperature for 1.5 hours, 8.30 ml (55.4 mmol) of 1,8-diazabicyclo[5.4.0]-7-undecene was added thereto, followed by stirring at room temperature for 18 hours. The solvent was evaporated under reduced pressure, and chloroform was added to the residue. The mixture was washed successively with 0.1N hydrochloric acid and a saturated sodium chloride aqueous solution. The organic layer was dried over anhydrous sodium sulfate, and the solvent was removed by evaporation under reduced pressure to give 6.07 g (quantitative) of the title compound as a yellow oily substance.

$^1$H-NMR (CDCl3) δ ppm: 1.27 (3H, t, J=7.3 Hz), 1.25–1.35 (1H, m), 1.35–1.45 (1H, m), 1.46 (9H, s), 1.90–2.05 (2H, m), 4.10–4.20 (2H, m), 6.00 (1H, d, J=15.6 Hz), and 6.90 (1H, ddd, J=15.6, 8.8, 1.5 Hz).

Reference Example F

Ethyl 3-(Cis-2-t-butoxycarbonylcyclopropyl)-3-nitroethylpropionate

To 60 ml of a nitromethane solution of 6.07 g (25.2 mmol) of ethyl 3-(cis-2-t-butoxycarbonylcyclopropyl)acrylate was added 3.48 ml (27.7 mmol) of tetramethylguanidine at room temperature, and the mixture was stirred for 6 hours. To the reaction mixture was further added 0.32 ml (2.52 mmol) of tetramethylguanidine, followed by stirring for 18 hours. The solvent was evaporated under reduced pressure, and the residue was purified by silica gel column chromatography (hexane:ethyl acetate=85:15) to give 6.536 g (85.9%) of the title compound as a pale yellow oily substance.

$^1$H-NMR (CDCl$_3$) δ ppm: 0.95–1.10 (2H, m), 1.20–1.30 (4H, m), 1.46 and 1.48 (9H, s each), 1.65–1.80 (1H, m), 2.40–2.70 (2H, m), 2.70–2.80 (1H, m), 4.10–4.20 (2H, m), and 4.45–4.55 and 4.60–4.75 (2H, m each)

Reference Example G 3-(Cis-2-t-butoxycarbonylcyclopropyl)pyrrolidin-2-one

To 200 ml of a methanol solution of 6.536 g (21.7 mmol) of ethyl 3-(cis-2-t-butoxycarbonylcyclopropyl)-3-nitroethylpropionate were added 5 g of 10% palladium-on-carbon and 13.68 g (217 mmol) of ammonium formate at room temperature, and the mixture was stirred at the same temperature for 1.5 hours. After completion of the reaction, the solvent was evaporated under reduced pressure. Water was added to the residue, and the mixture was extracted with chloroform. The organic layer was dried over anhydrous sodium sulfate, and the solvent was evaporated under reduced pressure to give a crude amine.

A toluene solution (150 ml) of the resulting crude amine was heated at 110 to 120° C. for 2 hours. The solvent was evaporated under reduced pressure to give 4.89 g (quantitative) of the title compound as yellow crystals.

$^1$H-NMR (CDCl$_3$) δ ppm: 0.90–1.10 (2H, m), 1.20–1.35 (1H, m), 1.45 (9H, s), 1.65–1.75 (1H, m), 2.10–2.70 (3H, m), 3.10–3.20 and 3.20–3.30 (1H, m each), 3.35–3.45 and 3.55–3.65 (1H, m each), and 6.06 (1H, brs).

Reference Example H

1-Benzyl-3-(cis-2-t-butoxycarbonylcyclopropyl)pyrrolidin-2-one

To 30 ml of a dimethylformamide solution of 2.288 g (10.2 mmol) of 3-(cis-2-t-butoxycarbonylcyclopropyl)pyrrolidin-2-one was added 406.2 mg (10.2 mmol) of sodium hydride under cooling with ice, followed by stirring at room temperature for 1.5 hours. Then, 1.81 ml (15.3 mmol) of benzyl chloride was added thereto dropwise, followed by stirring for 2.5 hours. After completion of the reaction, water was added to the reaction mixture, and the mixture was extracted with ethyl acetate, and the organic layer was washed with water and a saturated sodium chloride aqueous solution. The organic layer was dried over anhydrous sodium sulfate, and the solvent was removed by evaporation under reduced pressure. The residue was purified by silica gel column chromatography (hexane:ethyl acetate=7:3) to give 1.121 g (35.0%) of 1-benzyl-3-(2-t-butoxycarbonylcyclopropyl)pyrrolidin-2-one (isomer A: an isomer attributed to the steric configuration of the cyclopropyl group bonded to the carbon atom of the pyrrolidine ring) as a colorless solid. The column was then eluted with hexane:ethyl acetate=1:1 to give 670.9 mg (20.9%) of 1-benzyl-3-(cis-2-t-butoxycarbonylcyclopropyl)pyrrolidin-2-one (isomer B: an isomer attributed to the steric configuration of the cyclopropyl group bonded to the carbon atom of the pyrrolidine ring) as a colorless solid.

Isomer A $^1$H-NMR (CDCl$_3$) δ ppm: 0.85–1.00 (2H, m), 1.10–1.25 (1H, m), 1.45 (9H, s), 1.65–1.75 (1H, m), 2.25 (1H, dd, J=16.1, 6.4 Hz), 2.35–2.45 (1H, m), 2.50 (1H, dd, J=16.1, 8.8 Hz), 3.08 (1H, dd, J=9.8, 5.9 Hz), 3.43 (1H, t, J=8.8 Hz), 4.45 (1H, d, J=14.7 Hz), 4.46 (1H, d, J=14.7 Hz), and 7.20–7.40 (5H, m).

Isomer B $^1$H-NMR (CDCl$_3$) δ ppm: 0.90–1.00 (1H, m), 1.00–1.10 (1H, m), 1.15–1.25 (1H, m), 1.37 (9H, s), 1.55–1.65 (1H, m), 2.33 (1H, dd, J=16.1, 7.3 Hz), 2.35–2.45 (1H, m), 2.68 (1H, dd, J=16.1, 8.3 Hz), 2.99 (1H, dd, J=9.3, 5.9 Hz), 3.20 (1H, dd, J=9.3, 7.8 Hz), 4.39 (1H, d, J=14.7 Hz), 4.48 (1H, d, J=14.7 Hz), and 7.20–7.40 (5H, m).

Reference Example I

1-Benzyl-3-(cis-2-t-butoxycarbonylcyclopropyl)pyrrolidine-2-thione (Isomer A)

To 40 ml of a toluene solution of 1.990 g (6.31 mmol) of 1-benzyl-3-(cis-2-t-butoxycarbonylcyclopropyl)pyrrolidin-2-one (isomer A) was added 1.378 g (3.41 mmol) of a Lawson's reagent, and, the mixture was stirred at 50 to 60° C. for 1.5 hours. After completion of the reaction, the reaction mixture was subjected to silica gel column chromatography (hexane:ethyl acetate=7:3) to give 1.707 g (81.6%) of the title compound (isomer A) as a pale yellow solid.

$^1$H-NMR (CDCl$_3$) δ ppm: 0.80–0.90 (1H, m), 0.90–1.00 (1H, m), 1.10–1.20 (1H, m), 1.45 (9H, s), 1.65–1.75 (1H, m), 2.40–2.55 (1H, m), 2.90 (1H, dd, J=17.6, 5.4 Hz), 3.12 (1H, dd, J=17.6, 8.3 Hz), 3.41 (1H, dd, J=11.2, 5.4 Hz), 3.75 (1H, dd, J=11.2, 7.8 Hz), 4.97 (1H, d, J=14.2 Hz), 5.01 (1H, d, J=14.2 Hz), 7.30–7.40 (5H, m)

Reference Example J

1-Benzyl-3-(cis-2-t-butoxycarbonylcyclpropyl)pyrrolidine (Isomer A)

To 50 ml of an ethanol solution of 1.70 g (5.13 mmol) of 1-benzyl-3-(cis-2-t-butoxycarbonylcyclopropyl)

pyrrolidine-2-thione (isomer A) was added 14 ml of Raney nickel, followed by stirring at room temperature for 1.5 hours. Any insoluble matter was removed by filtration, and the solvent was evaporated under reduced pressure. Chloroform was added to the residue, and the mixture was washed with 10% aqueous ammonia. The organic layer was dried over anhydrous sodium sulfate, and the solvent was evaporated under reduced pressure to give 1.479 g (95.7%) of the title compound (isomer A) as a pale yellow oily substance.

$^1$H-NMR (CDCl$_3$) δ ppm: 0.85–0.95 (2H, m), 1.20–1.30 (1H, m), 1.44 (9H, s), 1.50–1.65 (2H, m), 1.85–1.95 (1H, m), 2.10–2.25 (1H, m), 2.40 (1H, dd, J=8.8, 5.9 Hz), 2.51 (1H, q, J=7.8 Hz), 2.62 (1H, dt, J=8.8, 5.4 Hz), 2.72 (1H, t, J=8.7 Hz), 3.59 (1H, d, J=12.7 Hz), 3.62 (1H, d, J=12.7 Hz), and 7.20–7.40 (5H, m).

Reference Example K

1-Benzyloxycarbonyl-3-(cis-2-t-butoxycarbonylcyclopropyl)pyrrolidine (Isomer A)

To 30 ml of a dichloromethane solution of 1.466 g (4.86 mmol) of 1-benzyl-3-(cis-2-t-butoxycarbonylcyclopropyl)pyrrolidine (isomer A) was added 1.39 ml (9.72 mmol) of benzyl chloroformate at room temperature, and the mixture was stirred at the same temperature for 15.5 hours, followed by heat-refluxing for 1 hour. To the reaction mixture was further added 0.70 ml (4.86 mmol) of benzyl chloroformate, followed by heat-refluxing for 1.5 hours. The solvent was evaporated under reduced pressure, and the residue was purified by silica gel column chromatography (hexane:ethyl acetate=7:3) to give 1.261 g (75.1%) of the title compound as a colorless oily substance.

$^1$H-NMR (CDCl$_3$) δ ppm: 0.90–1.00 (2H, m), 1.05–1.15 (1H m), 1.46 (9H, s), 1.60–1.70 (2H, m), 1.80–1.95 (1H, m), 2.20–2.30 (1H, m), 3.15–3.30 (1H, m), 3.30–3.40 (1H, m), 3.50–3.70 (2H, m), 5.14 (2H, s), and 7.25–7.40 (5H, m).

Reference Example L

1-Benzyloxycarbonyl-3-(cis-2-t-butoxycarbonylaminocyclopropyl)pyrrolidine (Isomer A)

To 10 ml of a dichloromethane solution of 1.252 g (3.62 mmol) of 1-benzyloxycarbonyl-3-(cis-2-t-butoxycarbonylcyclopropyl)pyrrolidine was added 5 ml of trifluoroacetic acid under cooling with ice, and the mixture was stirred at room temperature for 2 hours. After completion of the reaction, the solvent was removed by evaporation under reduced pressure. Toluene was added to the residue, followed by evaporation to obtain a crude carboxylic acid.

To 30 ml of a 2-methyl-2-propanol solution of the resulting crude carboxylic acid were added 0.781 ml (3.62 mmol) of diphenylphosphoric acid azide and 0.758 ml (5.43 mmol) of triethylamine, and the mixture was stirred at room temperature for 1 hour and then heated under reflux for 31 hours. After completion of the reaction, the solvent was evaporated under reduced pressure, and ethyl acetate was added to the residue. The mixture was washed successively with a 5% citric acid aqueous solution, a saturated sodium carbonate aqueous solution, and a saturated sodium chloride aqueous solution. The organic layer was dried over anhydrous sodium sulfate, and the solvent was evaporated under reduced pressure. The residue was purified by silica gel column chromatography (hexane:ethyl acetate=7:3) to give 6.67 g (64.1%) of ethyl 3-(cis-2-t-butoxycarbonylcyclopropyl)-3-oxopropionate as a yellow oily substance and 575.2 mg (44.0%) of 1-benzyloxycarbonyl-3-(cis-2-t-butoxycarbonylaminocyclopropyl)pyrrolidine (isomer A) as a colorless oily substance.

$^1$H-NMR (CDCl$_3$) δ ppm: 0.20–0.30 (1H, m), 0.75–0.95 (2H, m), 1.44 (9H, s), 1.70–1.90 (2H, m), 2.00–2.10 (1H, m), 2.65–2.75 (1H, m), 3.15–3.30 (1H, m), 3.30–3.40 (1H, m), 3.50–3.65 (2H, m), 4.50–4.65 (1H, brs), 5.13 (2H, s), and 7.30–7.40 (5H, m).

Reference Example M 3-(Cis-2-t-butoxycarbonylaminocyclopropyl)pyrrolidine (Isomer A)

To 15 ml of an ethanol solution of 547.3 mg (1.52 mmol) of 1-benzyloxycarbonyl-3-(cis-2-t-butoxycarbonylaminocyclopropyl)pyrrolidine (isomer A) was added 550 mg of 5% palladium-on-carbon, followed by shaking in a hydrogen stream (4 kg/cm$^2$) for 1.5 hours. The catalyst was removed by filtration, and the solvent was removed by evaporation under reduced pressure to give 343.6 mg (quantitative) of the title compound as a brown oily substance.

$^1$H-NMR (CDCl$_3$) δ ppm: 0.20–0.30 (1H, m), 0.75–0.95 (2H, m), 1.45 (9H, s), 1.55–1.75 (2H, m), 1.90–2.00 (1H, m), 2.60–2.70 (1H, m), 2.70–2.80 (1H, m), 2.90–3.00 (1H, m), 3.00–3.15 (2H, m), and 4.70–4.80 (1H, brs).

Reference Example N

1-Benzyl-3-(cis-2-t-butoxycarbonylcyclopropyl)pyrrolidine-2-thione (Isomer B)

To 30 ml of a toluene solution of 1.534 g (4.86 mmol) of 1-benzyl-3-(cis-2-t-butoxycarbonylcyclopropyl)pyrrolidin-2-one (isomer B) was added 1.062 g (2.62 mmol) of a Lawson's reagent, followed by stirring at 50 to 60° C. for 1.5 hours. After completion of the reaction, the reaction mixture was subjected to silica gel column chromatography (hexane:ethyl acetate=7:3) to give 1.198 g (74.3%) of the title compound as a pale yellow solid.

$^1$H-NMR (CDCl$_3$) δ ppm: 0.90–1.00 (1H, m), 1.00–1.10 (1H, m), 1.10–1.20 (1H, m), 1.35 (9H, s), 1.55–1.65 (1H m), 2.40–2.50 (1H, m), 2.97 (1H, dd, J=18.1, 6.3 Hz), 3.25–3.35 (2H, m), 3.52 (1H, dd, J=11.2, 6.8 Hz), 4.92 (1H, d, J=14.2 Hz), 5.01 (1H, d, J=14.2 Hz), 7.25–7.40 (5H, m).

Reference Example O

1-Benzyl-3-(cis-2-t-butoxycarbonylcyclopropyl)pyrrolidine (Isomer B)

To 50 ml of an ethanol solution of 1.19 g (3.59 mmol) of 1-benzyl-3-(cis-2-t-butoxycarbonylcyclopropyl)pyrrolidine-2-thione (isomer B) was added 10 ml of Raney nickel, followed by stirring at room temperature for 30 minutes. The insoluble matter was filtered of f, and the solvent was evaporated under reduced pressure. Chloroform was added to the residue, and the mixture was washed with 10% aqueous ammonia. The organic layer was dried over anhydrous sodium sulfate, and the solvent was evaporated under reduced pressure to give 929.0 mg (85.8%) of the title compound as a pale yellow oily substance.

$^1$H-NMR (CDCl$_3$) δ ppm: 0.85–0.95 (2H, m), 1.15–1.30 (1H, m), 1.38 (9H, s), 1.55–1.70 (2H, m), 2.05–2.25 (2H, m), 2.25–2.35 (1H, m), 2.50–2.75 (3H, m), 3.56 (1H, d, J=12.7 Hz), 3.60 (1H, d, J=12.7 Hz), and 7.20–7.40 (5H, m).

Reference Example P

1-Benzyloxycarbonyl-3-(cis-2-t-butoxycarbonylcyclopropyl)vyrrolidine (Isomer B)

To 15 ml of a dichloromethane solution of 922.6 mg (3.06 mmol) of 1-benzyl-3-(cis-2-t-butoxycarbonylcyclopropyl) pyrrolidine (isomer B) was added 0.874 ml (6.12 mmol) of benzyl chloroformate at room temperature, followed by stirring at the same temperature overnight. To the reaction mixture was further added 0.502 ml (3.52 mmol) of benzyl chloroformate, followed by stirring for 2 days. The solvent was evaporated under reduced pressure, and the residue was purified by silica gel column chromatography (hexane:ethyl acetate=7:3) to give 685.5 mg (64.8%) of the title compound as a colorless oily substance.

$^1$H-NMR (CDCl$_3$) δ ppm: 0.90–1.15 (3H, m), 1.43, 1.46 (9H, s each), 1.60–1.80 (2H, m), 2.00–2.15 (1H, m), 2.20–2.30 (1H, m), 3.05–3.20 (1H, m), 3.30–3.50 (2H, m), 3.50–3.65 (1H, m), 5.10–5.20 (2H, m), and 7.25–7.40 (5H, m).

Reference Example Q

1-Benzyloxycarbonyl-3-(cis-2-t-butoxycarbonylaminocyclopropyl)pyrrolidine (Isomer B)

To 3 ml of a dichloromethane solution of 685.5 mg (1. 98 mmol) of 1-benzyloxycarbonyl-3-(cis-2-t-butoxycarbonylcyclopropyl)pyrrolidine (isomer B) was added 3 ml of trifluoroacetic acid under cooling with ice, followed by stirring at room temperature for 1.5 hours. After completion of the reaction, the solvent was evaporated under reduced pressure, and toluene was added to the residue, followed by evaporation to obtain a crude carboxylic acid.

To 20 ml of a 2-methyl-2-propanol solution of the resulting crude carboxylic acid were added 0.411 ml (1.98 mmol) of diphenylphosphoric acid azide and 0.399 ml (2.97 mmol) of triethylamine, and the mixture was stirred at room temperature for 1.5 hours and then heated under reflux for 16 hours. After completion of the reaction, the solvent was removed by evaporation under reduced pressure, and ethyl acetate was added to the residue. The mixture was washed successively with a 5% citric acid aqueous solution, a saturated sodium carbonate aqueous solution, and a saturated sodium chloride aqueous solution. The organic layer was dried over anhydrous sodium sulfate, and the solvent was evaporated under reduced pressure. The residue was purified by silica gel column chromatography (hexane:ethyl acetate=7:3) to give 345.2 mg (48.3%) of the title compound as a colorless oily substance.

$^1$H-NMR (CDCl$_3$) δ ppm: 0.20–0.35 (1H, m), 0.75–0.85 (1H, m), 0.90–1.00 (1H, m), 1.40 (9H, s), 1.70–1.85 (2H, m), 1.95–2.10 (1H, m), 2.60–2.70 (1H, m), 3.10–3.25 (1H, m), 3.30–3.40 (1H, m), 3.50–3.70 (2H, m), 4.50–4.65 (1H, brs), 5.05–5.20 (2H, m), and 7.25–7.40 (5H, m).

Reference Example R 3-(Cis-2-t-butoxycarbonylaminocyclopropyl) pyrrolidine (Isomer B)

To 10 ml of an ethanol solution of 340.4 mg (0.94 mmol) of 1-benzyloxycarbonyl-3-(cis-2-t-butoxycarbonylaminocyclopropyl)pyrrolidine was added 350 mg of 5% palladium-on-carbon, and the mixture was shaken in a hydrogen stream (3.5 kg/cm$^2$) for 1.5 hours. The catalyst was removed by filtration, and the solvent was evaporated under reduced pressure to give 213.0 mg (99.7%) of the title compound as a colorless solid.

$^1$H-NMR (CDCl$_3$) δ ppm: 0.20–0.30 (1H, m), 0.75–1.00 (2H, m), 1.45 (9H, s), 1.60–1.80 (2H, m), 1.90–2.05 (1H, m), 2.60–2.80 (2H, m), 2.80–3.20 (3H, m), and 4.65–4.80 (1H, m).

Reference Example S (1S,2R)-t-Butyl Cis-2-methoxycarbonylcyclopropanecarboxylate To 120 ml of anhydrous tetrahydrofuran solution of 11.38 g (79.0 mmol) of (−)-(1S,2R)-2-methoxycarbonylcyclopropanecarboxylic acid were added 1.93 g (15.80 mmol) of dimethylaminopyridine and 22.41 g (102.67 mmol) of di-t-butyl dicarbonate at room temperature, and the mixture was stirred at the same temperature for 18 hours. After completion of the reaction, the solvent was evaporated under reduced pressure, and ethyl acetate was added to the residue. The mixture was washed successively with 0.5N hydrochloric acid, water, and a saturated sodium chloride aqueous solution. The organic layer was dried over anhydrous sodium sulfate, and the solvent was evaporated under reduced pressure to give 15.81 g (quantitative) of the title compound as a brown oily substance.

$^1$H-NMR (CDCl$_3$) δ ppm: 1.17 (1H, dt, J=8.3, 4.9 Hz), 1.44 (9H, s), 1.55–1.65 (1H, m), 1.95–2.05 (2H, m), and 3.69 (3H, s).

Reference Example T (1R,2S)-Cis-2-t-butoxycarbonylcyclopropanecarboxylic Acid To 150 ml of a methanol solution of 15.81 g (79.0 mmol) of (1S,2R)-t-butyl2-methoxycarbonylcyclopropanecarboxylate was added 50 ml of an aqueous solution of 6.77 g (102.6 mmol) of potassium hydroxide under ice-cooling, followed by stirring at room temperature overnight. After completion of the reaction, the solvent was removed by evaporation under reduced pressure. Water was added to the residue, followed by washing with diethyl ether. The aqueous solution was adjusted to a p of 2 to 3 with concentrated hydrochloric acid and extracted with ethyl acetate. The organic layer was dried over anhydrous sodium sulfate, and the solvent was evaporated under reduced pressure to give 14.71 g (quantitative) of the title compound as a pale yellow solid.

$^1$H-NMR (CDCl$_3$) δ ppm: 1.25–1.35 (1H, m), 1.44 (9H, s), 1.60–1.65 (1H, m), and 2.00–2.10 (2H, m).

Reference Example U

Ethyl 3-[(1R,2S)-2-t-butoxycarbonylcyclopropyl]-3-oxopropionate

To 170 ml of an anhydrous tetrahydrofuran solution of 14.71 g (79.0 mmol) of (1R,2S)-2-t-butoxycarbonylcyclopropanecarboxylic acid was added 16.49 g (90.6 mmol) of 1,1-carbonyldiimidazole under cooling with ice, and the mixture was stirred at room temperature for 1.5 hours. The solvent was removed by evaporation under reduced pressure. To 60 ml of an anhydrous tetrahydrofuran solution of the resulting residue was added 150 ml of an anhydrous tetrahydrofuran solution of 197.5 mmol of previously prepared magnesium monoethyl malonate, followed by stirring for 3 days. After completion of the reaction, the solvent was evaporated under reduced pressure. Ethyl acetate was added to the residue, and the mixture was washed successively with 0.5N hydrochloric acid, a saturated sodium hydrogencarbonate aqueous solution, and a saturated sodium chloride aqueous solution. The organic layer was dried over anhydrous sodium sulfate, and the solvent was evaporated under reduced pressure. The residue was purified by silica gel column chromatography (hexane:ethyl acetate=7:3) to give 18.53 g (91.8%) of the title compound as a colorless oily substance.

$^1$H-NMR (CDCl$_3$) δ ppm: 1.15–1.30 (4H, m), 1.42 (9H, s), 1.65–1.75 (1H, m), 2.00–2.10 (1H, m), 2.25–2.35 (1H, m), 3.50–3.65 (2H, m), and 4.15–5.25 (2H, m)

Reference Example V

Ethyl 3-[(1R,2S)-2-t-Butoxycarbonylcylcopropyl] acrylate

To 200 ml of a methanol solution of 18.48 g (72.1 mmol) of ethyl 3-[(1R,2S)-2-t-butoxycarbonylcyclopropyl]-3-oxopropionate was added 1.36 g (36.1 nmuol) of sodium borohydride at −10° C., followed by stirring at that temperature for 30 minutes. A saturated ammonium chloride aqueous solution was added thereto, and the reaction mixture was extracted with chloroform. The organic layer was dried over anhydrous sodium sulfate, and the solvent was evaporated under reduced pressure to give 18.62 g (quantitative) of a crude alcohol as a colorless oily substance.

To 400 ml of a dichloromethane solution of 18.62 g (72.1 mmol) of the crude alcohol were added 20.10 ml (144.2 mmol) of triethylamine and 7.25 ml (93.7 mmol) of methanesulfonyl chloride under cooling with ice. After stirring the mixture at the same temperature for 1.5 hours, 23.72 ml (158.6 mmol) of 1,8-diazabicyclo[5.4.0]-7-undecene was added thereto, followed by stirring at room temperature for 15 hours. The solvent was evaporated under reduced pressure, and chloroform was added to the residue. The mixture was washed successively with 0.1N hydrochloric acid, water ,and a saturated sodium chloride aqueous solution. The organic layer was dried over anhydrous sodium sulfate, and the solvent was evaporated under reduced pressure to give 17.33 g (quantitative) of the title compound as a yellow oily substance.

$^1$H-NMR (CDCl$_3$) δ ppm: 1.27 (3H, t, J=7.3 Hz), 1.25–1.35 (1H, m), 1.35–1.45 (1H, m), 1.45 (9H, s), 1.90–2.05 (2H, m), 4.10–4.25 (2H, m), 5.98 (1H, d, J=15.6 Hz), and 6.91 (1H, ddd, J=15.6, 8.8, 1.5 Hz)

Reference Example W

Ethyl 3-[(1R,2S)-2-t-Butoxycarbonylcyclopropyl]-3-nitroethylpropionate

To 150 ml of a nitromethane solution of 17.33 g (72.1 mmol) of ethyl 3-[(1R,2S)-2-t-butoxycarbonylcyclopropyl) acrylate was added 14.47 ml (115.4 mmol) of tetramethylguanidine at room temperature, and the mixture was stirred at 70° C. for 3.5 hours. The solvent was evaporated under reduced pressure, and the residue was purified by silica gel column chromatography (hexane:ethyl acetate= 85:15) to give 18.95 g (87.2%) of the title compound as a colorless oily substance.

$^1$H-NMR (CDCl$_3$) δ ppm: 0.95–1.15 (2H, m), 1.25–1.35 (4H, m), 1.46 and 1.48 (9H, s each), 1.65–1.80 (1H, m), 2.40–2.70 (2H, m), 2.70–2.85 (1H, m), 4.10–4.20 (2H, m), and 4.45–4.55 and 4.60–4.75 (2H, m each).

Reference Example X

3-[(1R,2S)-2-t-Butoxycarbonylcyclopropyl) pyrrolidin-2-one

To 600 ml of a methanol solution of 18.99 g (63.0 mmol) of ethyl 3-[(1R,2S)-2-t-butoxycarbonylcyclopropyl]-3-nitroethylpropionate were added about 5 g of 10% palladium-on-carbon, 7 g of 5% palladium-on-carbon, and 51.67 g (819 mmol) of ammonium formate at room temperature, and the mixture was stirred at the same temperature for 4 hours. After completion of the reaction, the solvent was evaporated under reduced pressure. Water was added to the residue, followed by extraction with chloroform. The organic layer was dried over anhydrous sodium sulfate, and the solvent was evaporated under reduced pressure to give 14.67 g (85.8%) of a crude amine.

A toluene solution (500 ml) of 14.67 g of the resulting crude amine was heated at 110 to 120° C. for 1.5 hours. The solvent was evaporated under reduced pressure, and the residue was purified by silica gel column chromatography (chloroform:methanol=98:2) to give 10.38 g of a mixture of 3-[(1R,2S)-2-t-butoxycarbonylcyolopropyl]pyrrolidin-2-one and 3-[1R,2S)-2-t-butoxycarbonylcylcopropyl]-1-hydroxypyrrolidin-2-one and 2.08 g of 3-[(1R,2S)-2-t-butoxycarbonylcyclopropyl]-1-hydroxypyrrolidin-2-one as colorless crystals.

To 100 ml of a solution of 1.85 g of the resulting 3-[(1R,2S)-2-t-butoxycarbonylcyclopropyl]-1-hydroxypyrrolidin-2-one in a 3:1 mixed solvent of methanol and water was added 4.45 ml of a titanium trichloride solution at room temperature while maintaining the reaction mixture neutral by addition of a 1N sodium hydroxide aqueous solution, followed by stirring at the same temperature for 1.5 hours. After completion of the reaction, water was added to the reaction mixture, and the mixture was extracted with ethyl acetate. The organic layer was dried over anhydrous sodium sulfate, and the solvent was evaporated under reduced pressure to give 1.53 g (88.4%) of 3-[(1R,2S)-2-t-butoxycarbonylcyclopropyl]pyrrolidin-2-one.

In the same manner, 7.30 g of 3-[(1R,2S)-2-t-butoxycarbonylcyclopropyl]pyrrolidin-2-one was obtained from 9.49 g of the mixture of 3-((1R,2S)-2-t-butoxycarbonyl-cyclopropyl]pyrrolidin-2-one and 3-[(1R, 2S)-2-t-butoxycarbonylcyclopropyl]-1-hydroxypyrrolidin-2-one.

$^1$H-NMR (CDCl$_3$) δ ppm: 0.95–1.10 (2H, m), 1.20–1.35 (1H, m), 1.45 (9H, s), 1.65–1.75 (1H, m), 2.05–2.60 (3H, m), 3.10–3.20, 3.20–3.30 (1H, m each), 3.35–3.45, 3.55–3.65 (1H, m each), and 5.90–6.10 (1H, m).

Reference Example Y

1-Benzyl-3-[(1R,2S)-2-t-butoxy-carbonylcyclopropyl]pyrrolidon-2-one

A solution (100 ml) of 8.816 g (39.1 mmol) of 3-[(1R, 2S)-2-t-butoxycarbonylcylcopropyl]pyrrolidin-2-one in a 3:2 mixed solvent of tetrahydrofuran and dimethylformamide was added dropwise to 20 ml of a suspension of 1.72 g (43.0 mmol) of sodium hydride in dimethylformamide while cooling with ice, and the mixture was stirred at room temperature for 1.5 hours. Then, 40 ml of a tetrahydrofuran solution of 6.76 ml (58.7 mmol) of benzyl chloride was added dropwise thereto, followed by stirring for 3 hours. After completion of the reaction, a saturated ammonium chloride aqueous solution was added thereto, followed by evaporation under reduced pressure. Water was added to the residue, and the mixture was extracted with ethyl acetate. The organic layer was washed with water and then with a saturated sodium chloride aqueous solution. The organic layer was dried over anhydrous sodium sulfate, and the solvent was evaporated under reduced pressure. The residue was purified by silica gel column chromatography (hexane:ethyl acetate=7:3) to give 5.710 g (44.8%) of 1-benzyl-3-[(1R,2S)-2-t-butoxycarbonylcyclopropyl]pyrrolidin-2-one (isomer $A^1$) as a colorless solid. Then, the column was eluted with a 1:1 mixed solvent of hexane and ethyl acetate to give 3.959 g (31.1%) of 1-benzyl-3-[(1R,2S)-2-t-butoxycarbonylcyclopropyl]pyrrolidin-2-one (isomer $B^1$) as a pale yellow oily substance.

Isomer $A^1$ $^1$H-NMR (CDCl$_3$) δ ppm: 0.85–1.00 (2H, m), 1.10–1.20 (1H, m), 1.45 (9H, s), 1.65–1.75 (1H, m), 2.25 (1H, dd, J=16.1, 6.3 Hz), 2.35–2.45 (1H, m), 2.50 (1H, dd, J=16.1, 8.8 Hz), 3.08 (1H, dd, J=9.8, 5.9 Hz), 3.43 (1H, dd, J=9.8, 7.8 Hz), 4.45 (1H, d, J=14.7 Hz), 4.46 (1H, d, J=14.7 Hz), and 7.20–7.40 (5H, m)

Isomer $B^1$ $^1$H-NMR (CDCl$_3$) δ ppm: 0.90–1.00 (1H, m), 1.00–1.05 (1H, m), 1.10–1.25 (1H, m), 1.37 (9H, s), 1.55–1.65 (1H, m), 2.33 (1H, dd, J=16.1, 7.3 Hz), 2.35–2.50 (1H, m), 2.67 (1H, dd, J=16.1, 8.3 Hz), 2.99 (1H, dd, J=9.8, 6.3 Hz), 3.21 (1H, dd, J=9.8, 7.8 Hz), 4.40 (1H, d, J=14.7 Hz), 4.48 (1H, d, J=14.7 Hz), and 7.20–7.40 (5H, m)

$[α]_D^{22}$+75.980 (c=1.045, CHCl$_3$)

Reference Example Z

1-Benzyl-3-[(1R,2S)-2-t-butoxycarbonyl-cyclopropyl]pyrrolidine-2-thione (Isomer $B^1$)

To 80 ml of a toluene solution of 3.999 g (12.69 mmol) of 1-benzyl-3-[(1R,2S)-2-t-butoxycarbonylcyclopropyl]-pyrrolidin-2-one (isomer $B^1$) was added 2.769 g (6.85 mmol) of a Lawson's reagent, and the mixture was stirred at 50 to 60° C. for 1 hour and 40 minutes. After completion of the reaction, the reaction mixture was subjected to silica gel column chromatography (hexane:ethyl acetate-4:1) to give 4.044 g (96.2%) of the title compound as a pale yellow solid.

$^1$H-NMR (CDCl$_3$) δ ppm: 0.90–1.00 (1H, m), 1.00–1.10 (1H, m), 1.10–1.20 (1H, m), 1.35 (9H, s), 1.55–1.65 (1H, m), 2.40–2.55 (1H, m), 2.97 (1H, dd, J=17.6, 6.4 Hz), 3.25–3.35 (2H, m), 3.52 (1H, dd, J=11.2, 7.8 Hz), 4.92 (1H, d, J=14.2 Hz), 5.01 (1H, d, J=14.2 Hz), and 7.25–7.40 (5H, m).

Reference Example AA

1-Benzyl-3-[(1R,2S)-2-t-butoxy-carbonylcyclopropyl]pyrrolidine (Isomer $B^1$)

To 60 ml of an ethanol solution of 4.040 g (12.19 mmol) of 1-benzyl-3-[(1R,2S)-2-t-butoxycarbonylcyclopropyl] pyrrolidine-2-thione (isomer $B^1$) was added 20 ml of Raney nickel, followed by stirring at room temperature for 40 minutes. Any insoluble matter was removed by filtration, and the solvent was evaporated under reduced pressure. Chloroform was added to the residue, and the mixture was washed with 10% aqueous ammonia. The organic layer was dried over anhydrous sodium sulfate, and the solvent was evaporated under reduced pressure to give 2.988 g (81.3%) of the title compound as a colorless oily substance.

$^1$H-NMR (CDCl$_3$) δ ppm: 0.85–1.00 (2H, m), 1.15–1.30 (1H, m), 1.38 (9H, s), 1.55–1.70 (2H, m), 2.00–2.25 (2H, m), 2.30 (1H, dd, J=9.3, 5.9 Hz), 2.50–2.65 (3H, m), 3.56 (1H, d, J=12.7 Hz), 3.60 (1H, d, J=12.7 Hz), and 7.20–7.35 (5H, m).

Reference Example BB

1-Benzyloxycarbonyl-3-[(1R,2S)-2-t-butoxycarbonylcyclopropyl]pyrrolidine (Isomer $B^1$)

To 50 ml of a dichloromethane solution of 2.984 g (9.90 mmol) of 1-benzyl-3-[(1R,2S)-2-t-butoxycarbonylcyclopropyl]pyrrolidine (isomer $B^1$) was added 2.83 ml (19.82 mmol) of benzyl chloroformate at room temperature, and the mixture was stirred at the same temperature for 14 hours. To the reaction mixture was further added 1.98 ml (13.86 mmol) of benzyl chloroformate, followed by refluxing for 2 hours. The solvent was evaporated under reduced pressure, and the residue was purified by silica gel column chromatography (hexane:ethyl acetate=7:3) to give 2.188 g (64.0%) of the title compound as a colorless oily substance.

$^1$H-NMR (CDCl$_3$) δ ppm: 0.90–1.05 (2H, m), 1.05–1.15 (1H, m), 1.43 and 1.46 (9H, s each), 1.60–1.80 (2H, m), 2.00–2.15 (1H, m), 2.20–2.30 (1H, m), 3.05–3.20 (1H, m), 3.30–3.40 (1H, m), 3.40–3.50 (1H, m), 3.50–3.65 (1H, m), 5.05–5.20 (2H, m), and 7.25–7.40 (5H, m).

Reference Example CC

1-Benzyloxycarbonyl-3-[(1S,2S)-2-t-butoxycarbonylaminocyclopropyl]pyrrolidine (Isomer $B^1$)

To 10 ml of a dichloromethane solution of 2.183 g (6.32 mmol) of 1-benzyloxycarbonyl-3-[(1R,2S)-2-t-butoxycarbonylcyclopropyl]pyrrolidine (isomer $B^1$) was added 8 ml of trifluoroacetic acid under cooling with ice, and the mixture was stirred at room temperature for 1.5 hours. After completion of the reaction, the solvent was evaporated under reduced pressure. Toluene was added to the residue and evaporated under reduced pressure to obtain a crude carboxylic acid.

To 60 ml of a solution of the resulting crude carboxylic acid in 2-methyl-2-propanol were added 1.36 ml (6.32 mmol) of diphenylphosphoric acid azide and 1.32 ml (9.48 mmol) of triethylamine, and the mixture was stirred at room temperature for 1.5 hours and then heated under reflux for 35 hours. After completion of the reaction, the solvent was evaporated under reduced pressure. Ethyl acetate was added to the residue, and the mixture was washed successively with a 5% citric acid aqueous solution, a saturated sodium carbonate aqueous solution, and a saturated sodium chloride aqueous solution. The organic layer was dried over anhydrous sodium sulfate, and the solvent was evaporated under reduced pressure. The resulting residue was purified by silica gel column chromatography (hexane:ethyl acetate= 7:3) to give 950.3 mg (41.7%) of the title compound as a colorless oily substance.

$^1$H-NMR (CDCl$_3$) δ ppm: 0.20–0.35 (1H, m), 0.75–0.90 (1H, m), 0.90–1.00 (1H, m), 1.40 (9H, s), 1.70–1.85 (2H, m), 1.95–2.10 (1H, m), 2.60–2.70 (1H, m), 3.15–3.25 (1H, m), 3.30–3.40 (1H, m), 3.50–3.70 (2H, m), 4.50–4.65 (1H, brs), 5.05–5.15 (2H, m), and 7.25–7.40 (5H, m).

$[α]_D^{23}$+36.820 (c=1.950, CHCl$_3$)

Reference Example DD

3-[(1S,2S)-2-t-Butoxycarbonylaminocyclopropyl]pyrrolidine (Isomer $B^1$)

To 25 ml of an ethanol solution of 911.3 mg (2.53 mmol) of 1-benzyloxycarbonyl-3-[(1S,2S)-2-t- butoxycarbonylaminocyclopropyl]pyrrolidine (isomer B¹) was added 900 mg of 5% palladium-on-carbon, and the mixture was shaken in a hydrogen stream (4.5 kg/cm²) for 1.5 hours. To the reaction mixture was added 100 mg of 5% palladium-on-carbon, followed by shaking in a hydrogen stream (4.0 kg/cm²) for 1 hour. The catalyst was removed by filtration, and the solvent was removed by evaporation under reduced pressure to give 572.2 mg (quantitative) of the title compound as a colorless solid.

$^1$H-NMR (CDCl$_3$) δ ppm: 0.20–0.30 (1H, m), 0.80–1.00 (2H, m), 1.45 (9H, s), 1.65–1.85 (2H, m), 2.y00–2.10 (1H, m), 2.60–2.70 (1H, m), 2.80–2.95 (1H, m), 2.95–3.10 (1H, m), 3.15–3.25 (2H, m), 4.75–4.95 (1H, m).

The antimicrobial activity of the compound prepared in Example 3 is shown in Table 1 below.

TABLE 1

Antimicrobial Spectra

| Microorganism | MIC (µg/ml) |
| --- | --- |
| E. coli, NIHJ | ≦0.003 |
| S. flexneli, 2A 5503 | ≦0.003 |
| Pr. vulgaris, 08601 | 0.05 |
| Pr. mirabilis, IFO-3849 | 0.05 |
| Ser. marcescens, 10100 | 0.10 |
| Ps. aeruginosa, 32104 | 0.20 |
| Ps. aeruginosa, 32121 | 0.10 |
| Ps. maltophilia, IID-1275 | 0.05 |
| S. aureaus, 209P | ≦0.003 |
| S. epidermidis, 56500 | 0.006 |
| Str. pyogenes, G-36 | 0.006 |
| Str. faecalis, ATCC-19433 | 0.025 |
| S. aureus, 870307 | 0.025 |

INDUSTRIAL APPLICABILITY

The compound according to the present invention exhibits excellent activity and safety and is useful as an antimicrobial agent.

What is claimed is:

1. A compound represented by formula (I):

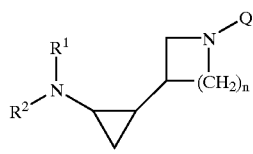

(I)

wherein R¹ and R² each independently represents a hydrogen atom or an alkyl group having 1 to 6 carbon atoms which may be substituted with one or more substituents selected from the group consisting of a hydroxyl group, a halogen atom, an alkylthio group having 1 to 6 carbon atoms, and an alkoxy group having 1 to 6 carbon atoms; n represents an integer of 1 to 3; Q represents a partial structure having formula:

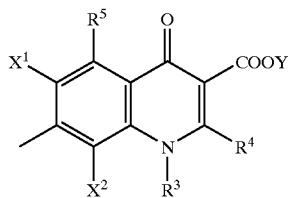

R⁴ represents a hydrogen atom or an alkylthio group having 1 to 6 carbon atoms;

R⁵ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxy group having 1 to 6 carbon atoms, in which the amino group may be substituted with one or more substituents selected from the group consisting of a formyl group, an alkyl group having 1 to 6 carbon atoms, and an acyl group having 2 to 5 carbon atoms;

X¹ represents a halogen atom or a hydrogen atom; and wherein X² and R³ are taken together with part of the mother skeleton to which they are bonded to form a cyclic structure having an oxygen atom as a ring constituting atom and/or may be substituted with an alkyl group having 1 to 6 carbon atoms; and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group having 1 to 6 carbon atoms in the alkyl moiety thereof; and the two substituents on the cyclopropane ring,

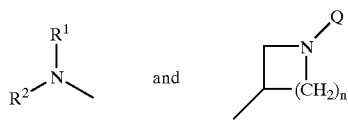

are in a cis-configuration, or a salt, a hydrate thereof, or a hydrate of the salt.

2. A compound represented by formula (I) according to claim 1, wherein X² and R³ are taken together with part of the mother skeleton to which they are bonded to form a 4- to 7-membered cyclic structure having an oxygen atom as a ring constituting atom and may be substituted with an alkyl group having 1 to 6 carbon atoms.

3. A compound according to claim 1, wherein Q in formula (I) is a 6-carboxy-9-fluoro-2,3-dihydro-3-(S)-methyl-7-oxo-7H-pyrido[1,2,3-de][1,4]benzoxazin-10-yl group, or a salt or hydrate thereof or a hydrate of the salt.

4. A compound according to claim 1, wherein Q in formula (I) is a 8-amino-6-carboxy-9-fluoro-2,3-dihydro-3-(S)-methyl-7-oxo-7H-pyrido[1,2,3-de][1,4]benzoxazin-10-yl group or a salt or hydrate thereof or a hydrate of the salt.

5. A compound according to claim 1, wherein n in formula (I) is 2, or a salt or hydrate thereof or a hydrate of the salt.

6. A compound according to claim 1, wherein both $R^1$ and $R^2$ in formula (I) are a hydrogen atom, or a salt or hydrate thereof or a hydrate of the salt.

7. A compound according to claim 1, wherein $X^1$ in formula (I) is a halogen atom, or a salt or hydrate thereof or a hydrate of the salt.

8. A compound according to claim 7, wherein $X^1$ in formula (I) is a fluorine atom, or a salt or hydrate thereof or a hydrate of the salt.

9. A compound according to claim 1, wherein the compound of formula (I) is a stereochemically pure compound, or a salt or hydrate thereof or a hydrate of the salt.

10. A pharmaceutical composition comprising an antimicrobially effective amount of any one of the compounds described in claims 3, 4, 5, 6, 7, 8, 9, or 1 hydrates thereof, salts thereof, and hydrates of the salts as an active ingredient and a pharmaceutically acceptable carrier.

* * * * *

UNITED STATES PATENT AND TRADEMARK OFFICE
CERTIFICATE OF CORRECTION

PATENT NO.    : 6,462,040 B1
DATED         : October 8, 2002
INVENTOR(S)   : Takemura Makoto et al.

It is certified that error appears in the above-identified patent and that said Letters Patent is hereby corrected as shown below:

<u>Title page,</u>
Item [73], Assignee, delete "Daiicho" and insert -- Daiichi --.

Signed and Sealed this

Eighth Day of April, 2003

JAMES E. ROGAN
*Director of the United States Patent and Trademark Office*